(12) United States Patent
Strydom et al.

(10) Patent No.: US 12,217,468 B2
(45) Date of Patent: Feb. 4, 2025

(54) SYSTEMS AND METHODS FOR SANITIZING SURFACES AND DEVICES AND METHODS FOR DETECTING AN ANTIMICROBIAL COATING

(71) Applicant: The Boeing Company, Chicago, IL (US)

(72) Inventors: Reuben Strydom, Brisbane (AU); Jason Armstrong, Brisbane (AU); David Corporal, Brisbane (AU); Nicola Vaisey, Brisbane (AU); Celeste De Mezieres, Brisbane (AU); Michael Monteiro, Brisbane (AU)

(73) Assignee: The Boeing Company, Arlington, VA (US)

( * ) Notice: Subject to any disclaimer, the term of this patent is extended or adjusted under 35 U.S.C. 154(b) by 415 days.

(21) Appl. No.: 17/690,245

(22) Filed: Mar. 9, 2022

(65) Prior Publication Data

US 2023/0290102 A1    Sep. 14, 2023

(51) Int. Cl.
*G06V 10/143*    (2022.01)
*A61L 2/10*    (2006.01)
(Continued)

(52) U.S. Cl.
CPC .............. *G06V 10/143* (2022.01); *A61L 2/10* (2013.01); *A61L 2/24* (2013.01); *A61L 2/26* (2013.01); *G06V 10/141* (2022.01); *G06V 10/60* (2022.01)

(58) Field of Classification Search
CPC .... G06V 10/143; G06V 10/141; G06V 10/60; A61L 2/10; A61L 2/24; A61L 2/26;
(Continued)

(56) References Cited

U.S. PATENT DOCUMENTS 10,428,020 B2    10/2019    Monteiro et al.
11,174,227 B2    11/2021    Monteiro et al.
(Continued)

FOREIGN PATENT DOCUMENTS

CN        102879015 B    * 11/2016    ............... G01J 1/18
WO     WO 2021/050355       3/2021

OTHER PUBLICATIONS

To, A.W.K., Paul, G. and Liu, D., 2013. Surface-type classification using RGB-D. IEEE Transactions on Automation Science and Engineering, 11(2), pp. 359-366.*

(Continued)

*Primary Examiner* — Zhitong Chen
(74) *Attorney, Agent, or Firm* — Walters & Wasylyna LLC

(57)    ABSTRACT

A device for detecting a coating applied to a surface includes a portable housing, a light source, a light detector, and a processing unit. The light source emits a first light having a first wavelength. The coating includes a fluorophore that re-emits a second light having a second wavelength, which is different than the first wavelength, in response to excitation by the first light. The light detector receives the second light re-emitted from the coating. The processing unit is adapted to determine a re-emission intensity of the second light and to determine a coverage metric of the coating based on the re-emission intensity of the second light. The coverage metric is then used to infer the efficacy of the coating.

20 Claims, 10 Drawing Sheets

(51) Int. Cl.
*A61L 2/24* (2006.01)
*A61L 2/26* (2006.01)
*G06V 10/141* (2022.01)
*G06V 10/60* (2022.01)

(58) Field of Classification Search
CPC ........... A61L 2/232; A01N 25/34; A01P 1/00; C09D 5/14; G01B 11/0658; G01N 21/643; G01N 21/6456; G01N 2021/646; G01N 2021/8433; G01N 2201/0221; G01N 21/8422; G01N 21/64; G01N 21/01; G01N 21/645; G01N 2021/6471; G01N 2201/121; H04N 23/71; H04N 23/74; G01J 1/4204
See application file for complete search history.

(56) References Cited

U.S. PATENT DOCUMENTS

| | | | |
|---|---|---|---|
| 2007/0275101 | A1 | 11/2007 | Lu et al. |
| 2017/0273307 | A1 | 9/2017 | Narine et al. |
| 2020/0361859 | A1 | 11/2020 | Monteiro et al. |
| 2021/0278343 | A1* | 9/2021 | Rosen ............... H04N 23/56 |
| 2021/0385317 | A1* | 12/2021 | Crosby ............... A61N 5/0624 |
| 2021/0404970 | A1* | 12/2021 | Poteet ............... G01N 21/643 |

OTHER PUBLICATIONS

J. GmbH, "3-Azido-7-hydroxycoumarin, Azide-containing Fluorescent Dyes—Jena Bioscience", Jenabioscience.com, 2020. [Online]. Available: https://www.jenabioscience.com/clickchemistry/click-reagents-by-chemistry/azide-reagents/fluorescent-dyes/clk-fa047-3-azido-7-hydroxycoumarin.

M. Alam, K. Wahid, R. Goel and K. Lukong, "Development of a low-cost and portable smart fluorometer for detecting breast cancer cells", Biomedical Optics Express, vol. 10, No. 2, p. 399, 2019. Available: 10.1364/boe.10.000399 [Accessed Jul. 27, 2020].

D. Shin, M. Pierce, A. Gillenwater, M. Williams and R. Richards-Kortum, "A Fiber-OpticFluorescence Microscope Using a Consumer-Grade Digital Camera for In Vivo Cellular Imaging", PLoS ONE, vol. 5, No. 6, p. e11218, 2010. Available: 10.1371/journal.pone.0011218.

"Fluorescence Spectrophotometer F-7100: Hitachi High-Tech Global", Hitachi-hightech.com, 2020. [Online]. Available: https://www.hitachi-hightech.com/global/product_detail/?pn=anaf7100.

NanoSight Range, 1st ed. Malvern Panalytical—Spectris Company, 2020, p. 11.

"Mini-Crime Scope Advanced (MCS-ADV)", Horiba.com, 2020. [Online]. Available: https://www.horiba.com/en_en/products/detail/action/show/Product/mini-crimescopeadvance-1704/.

"HandScope HS LED", Horiba.com, 2020. [Online]. Available: https://www.horiba.com/en_en/products/detail/action/show/Product/handscope-hs-led-1718//.

"Advanced Wound Care | Wound Healing Technologies | MolecuLight", MolecuLight, 2020. [Online]. Available: https://moleculight.com/.

"LED Spot Lights by LUMIMAX", lim-ag.com, 2020. [Online]. Available: https://www.iimag.com/en/lumimax/products/configurator/led-high-power-spots.html.

"Spectroline B-260 Rechargeable Battery Operated UV Lamp", Rfsales.com.au, 2020. [Online]. Available: https://www.rfsales.com.au/products/ultraviolet-light/uv-lamps/spectroline-b-260-rechargeable-battery-operated-uv-lamp/.

European Patent Office, Extended European Search Report, App. No. 23155413.0 (Jun. 22, 2023).

Dr. Michael Vergohl: "Deposition of Complex Bandpass Filters on Aspherical Lenses," Fraunhofer Institute for Surface Engineering and Thin Films IST, pp. 1-2 (Jan. 1, 2019).

Bobrin et al: "Water-Borne Nanocoating for Rapid Inactivation of SARS-CoV-2 and Other Viruses," ACS NANO, vol. 15, No. 9, pp. 14915-14927 (Aug. 23, 2021).

* cited by examiner

SYSTEMS AND METHODS FOR SANITIZING SURFACES AND DEVICES AND METHODS FOR DETECTING AN ANTIMICROBIAL COATING

FIELD

The present disclosure relates generally to sanitizing surfaces using antimicrobial coatings and, more particularly, to systems and methods for sanitizing surfaces and devices and methods for determining a coverage metric for an antimicrobial coating, which is used to infer efficacy of the antimicrobial coating.

BACKGROUND

Preventing transmission and growth of pathogens is an ongoing concern. Pandemics by viruses (e.g., SARS, SARS-CoV-2, Swine Flu and Ebola) have a major impact on the global economy. Prevention has conventionally focused on regular cleaning and sterilization of surfaces and improvements to air filtration systems. Cleaning is labor intensive and may not sufficiently sanitize a surface or prevent the spread of certain bacteria and viruses. Replacing and maintaining filters may be costly and impractical. Moreover, conventional techniques may be ineffective to reduce or stop growth of disease-causing microorganisms on surfaces. For example, bacteria and viruses can linger on surfaces for days and even up to a week.

A relatively recent alternative to conventional disease prevention is the use of surface contamination treatments produced for antibacterial and anti-viral applications. However, such antimicrobial surface coatings may degrade or wear over time, thus reducing effectiveness. Moreover, there is currently no practical technique to inspect a surface for the presence of an antimicrobial surface coating.

Accordingly, those skilled in the art continue with research and development efforts in the field of effectively reducing transmission and growth of microbes.

SUMMARY

Disclosed are examples of a device for detecting a coating applied to a surface, a system for sanitizing a surface, a method for detecting a coating applied to a surface, and a method for sanitizing a surface. The following is a non-exhaustive list of examples, which may or may not be claimed, of the subject matter according to the present disclosure.

In an example, the disclosed device includes a portable housing. The device includes a light source that is disposed within the portable housing and that emits a first light having a first wavelength. A coating, applied to the surface, includes a fluorophore that re-emits a second light having a second wavelength, which is different than the first wavelength, in response to excitation by the first light. The device includes a light detector that is disposed within the portable housing and that receives the second light re-emitted from the coating. The device includes a processing unit that is disposed within the portable housing and that is operatively coupled to the light detector. The processing unit is adapted to detect and process a re-emission intensity of the second light and to determine a coverage metric of the coating based on the re-emission intensity of the second light.

In an example, the disclosed system includes an antimicrobial coating that is appliable to a surface. The antimicrobial coating includes a fluorophore that, in response to excitation by a first light at a first wavelength, re-emits a second light at a second wavelength, which is different than the first wavelength. The system includes a device for detecting the antimicrobial coating on the surface. The device includes a portable housing. The device includes a light source that is disposed within the portable housing and that emits the first light at the first wavelength. The device includes a light detector that is disposed within the portable housing and that receives the second light re-emitted from the antimicrobial coating. The device includes a processing unit that is disposed within the portable housing and that is operatively coupled to the light detector. The processing unit is adapted to detect and process a re-emission intensity of the second light and to determine a coverage metric of the antimicrobial coating based on the re-emission intensity of the second light.

In an example, the method includes steps of: (1) directing a first light at a surface; (2) detecting the second light re-emitted from a coating, applied to the surface; and (3) detecting and processing a re-emission intensity of the second light.

In an example, the disclosed method includes steps of: (1) applying an antimicrobial coating to at least a portion of the surface, wherein the antimicrobial coating includes a fluorophore; (2) exciting the fluorophore in response to a first light, having a first wavelength, such that the antimicrobial coating re-emits a second light having a second wavelength, which is different than the first wavelength; (3) determining a re-emission intensity of the second light; and (4) determining a coverage metric of the antimicrobial coating based on the re-emission intensity of the second light.

Other examples of the disclosed device, system, and methods will become apparent from the following detailed description, the accompanying drawings, and the appended claims.

DETAILED DESCRIPTION

Figure 1A:
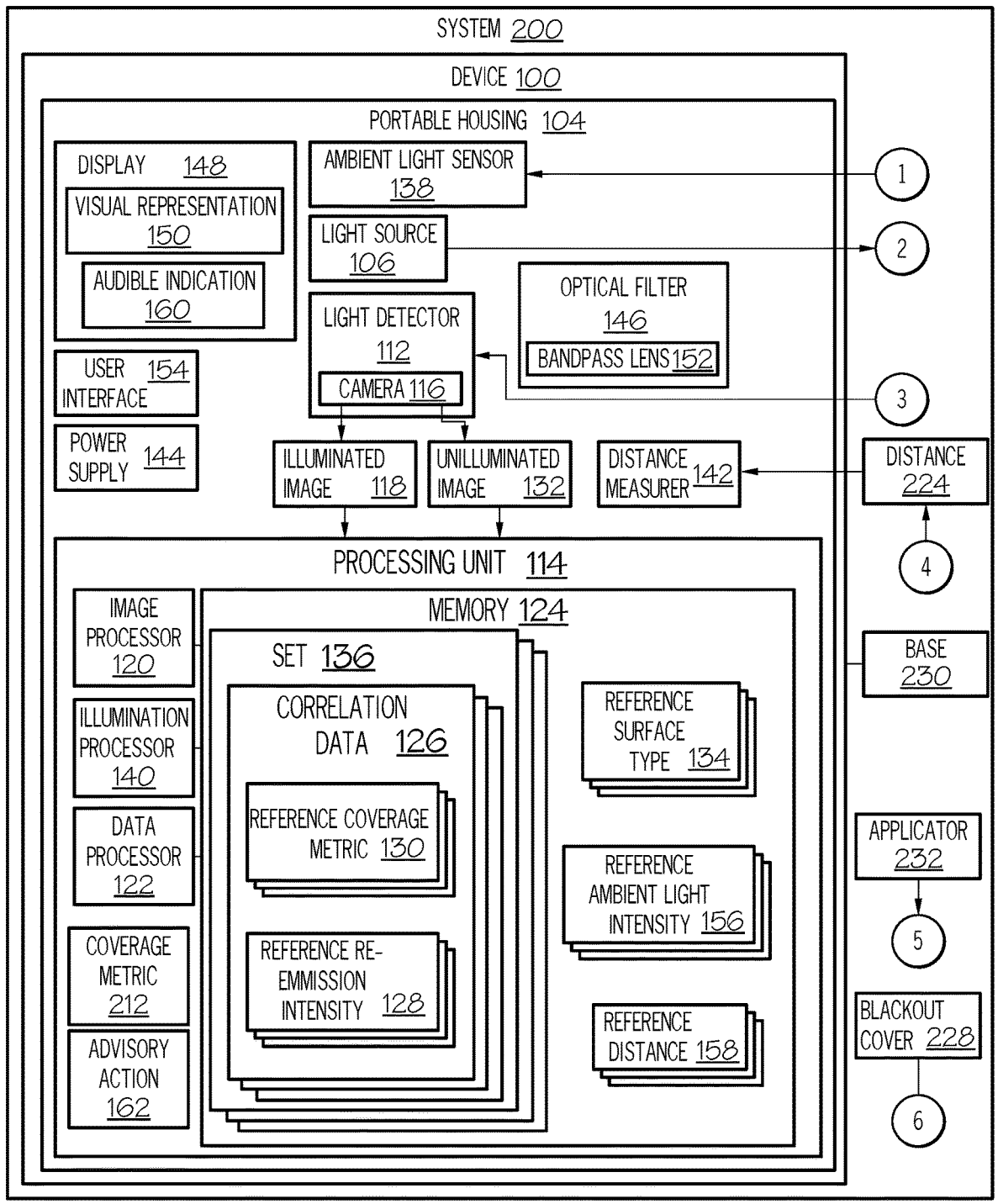
FIGS. 1A and 1B, in combination, are a schematic block diagram of an example of a system for sanitizing a surface and a device for detecting an antimicrobial coating on the surface.

Referring generally to FIGS. 1A, 1B and 2-6, by way of examples, the present disclosure is directed to a device 100 for detecting a coating 252 applied to a surface 214. In one or more examples, the coating 252 is an antimicrobial coating 202 that is applied to the surface 214 for the purpose of sanitizing the surface 214. In other examples, the coating 252 may be any one of various types of surface coatings or may have any one of various other purposes.

Generally, the device 100 is a fluorescent reader that is capable of exciting and detecting fluorescent light emitted by fluorescent materials in the coating 252 (e.g., the antimicrobial coating 202). While the examples of the device 100 disclosed herein refer to the excitation and generation of fluorescent light, in other examples, the device 100 may alternatively, or additionally, be capable of exciting and detecting phosphorescent light emitted by phosphorescent materials in the coating 252 (e.g., the antimicrobial coating 202). Therefore, throughout the present disclosure, the term "fluorescent light" may refer to either or both fluorescent light and phosphorescent light.

Generally, the device 100 provides a handheld and manually operated solution for quickly and efficiently inspecting the surface 214 and accurately detecting the presence of the coating 252 (e.g., the antimicrobial coating 202) on the surface 214. Utilization of the device 100 may ensure adequate and effective coverage of the coating 252 (e.g., the antimicrobial coating 202) on the surface 214 by detecting and recording the presence of a fluorescent chemical compound within the coating 252 (e.g., the antimicrobial coating 202). In one or more examples, the device 100 enables a user to quickly assess coverage of the coating 252 (e.g., the antimicrobial coating 202) during a surface inspection (e.g., scanning) operation by visually identifying light re-emitted from the fluorescent chemical compound in the coating 252 (e.g., the antimicrobial coating 202). In one or more examples, the device 100 enables sampling or recording of the light re-emitted from the fluorescent chemical compound in the coating 202 (e.g., the antimicrobial coating 202) and analysis of the light to qualitatively and/or quantitatively assess the coverage of the coating 252 (e.g., the antimicrobial coating 202).

For the purpose of the present disclosure, the antimicrobial coating 202 is a chemical compound that has antimicrobial properties effective at hindering or stopping the growth of microbes, reducing transmission of microbes, and/or reducing or killing microbes. Microbes can be viruses, bacteria, fungi, germs, pathogens, or other disease-causing micro-organisms.

Generally, the coating 252 (e.g., the antimicrobial coating 202) includes a polymer 250 that provides a base material. In one or more examples, the antimicrobial coating 202 also includes an antimicrobial agent 248 or other antimicrobial additives that are grafted, mixed, or chemically bonded to the polymer 250. The coating 252 (e.g., the antimicrobial coating 202) further includes a fluorophore 204 or a plurality of fluorophores. The fluorophore 204 is grafted, mixed, or chemically bonded to the polymer 250 and/or to the antimicrobial agent 248. The fluorophore 204 may be or include any suitable type of fluorescent material. Generally, the fluorophore 204 includes one or more chemical compounds that emit visible light after absorbing electromagnetic radiation. In one or more examples, the fluorophore 204 re-emits (e.g., is configured or adapted to re-emit) a second light 206 in response to excitation by a first light 108. The second light 206 has a second wavelength 208. The second wavelength 208 of the second light 206 is different than a first wavelength 110 of the first light 108. Accordingly, the light re-emitted from the fluorophore 204 of the coating 252 (e.g., the antimicrobial coating 202) can be used to qualitatively and/or quantitatively assess the coverage of the coating 252 (e.g., the antimicrobial coating 202) using the device 100.

In other examples, the coating 252 (e.g., the antimicrobial coating 202) includes a phosphorescent material that includes one or more chemicals that emit light (e.g., ultraviolet light) after exposure to electromagnetic radiation.

Throughout the present disclosure and accompanying figures, an example of the coating 252 (e.g., shown in FIG. 1B) is generally referred to as the antimicrobial coating 202 (e.g., as shown in FIGS. 1B, 2-4 and 6-8). However, reference to the antimicrobial coating 202 is not intended to necessarily limit the type and/or purpose of the coating 202.

Figure 2:
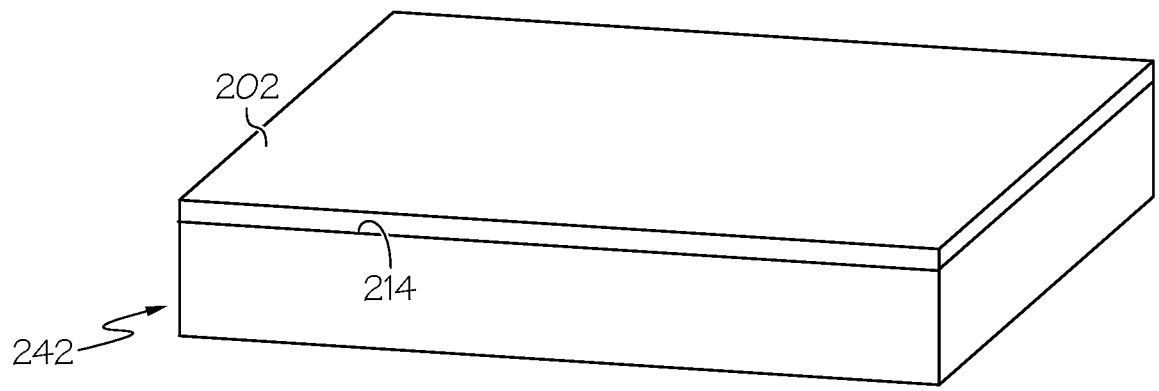
FIG. 2 is a schematic illustration of an example of a surface having the antimicrobial coating.

Referring now to FIG. 2, which schematically illustrates an example of a portion of an article 242. The article 242 includes the surface 214. At least a portion of the surface 214 is coated with the antimicrobial coating 202. For the purpose of the present disclosure, the terms "coated," "coating," and similar terms or variations of such terms refer to a material being applied to, attached to, or otherwise situated or located on a surface of an article.

Figure 3:
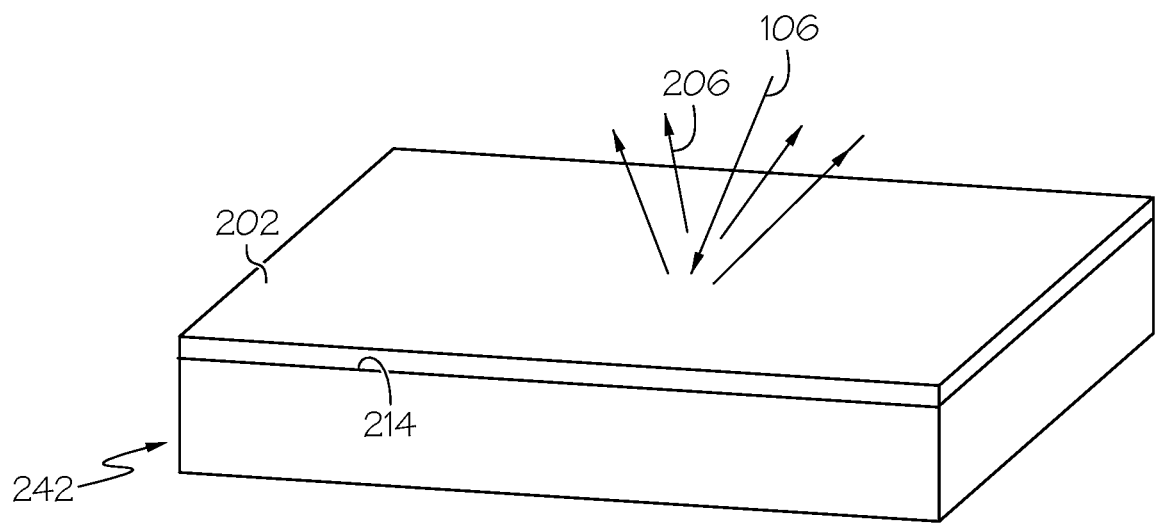
FIG. 3 is a schematic illustration of an example of the surface having the antimicrobial coating, shown in FIG. 2, excited by a first light and re-emitting a second light.

Referring now to FIG. 3, which schematically illustrates the article 242 of FIG. 2 after excitement of the fluorophore 204 of the antimicrobial coating 202, located on the surface 214, by the first light 108 and re-emission of the second light 206 from the fluorophore 204.

Figure 1B:
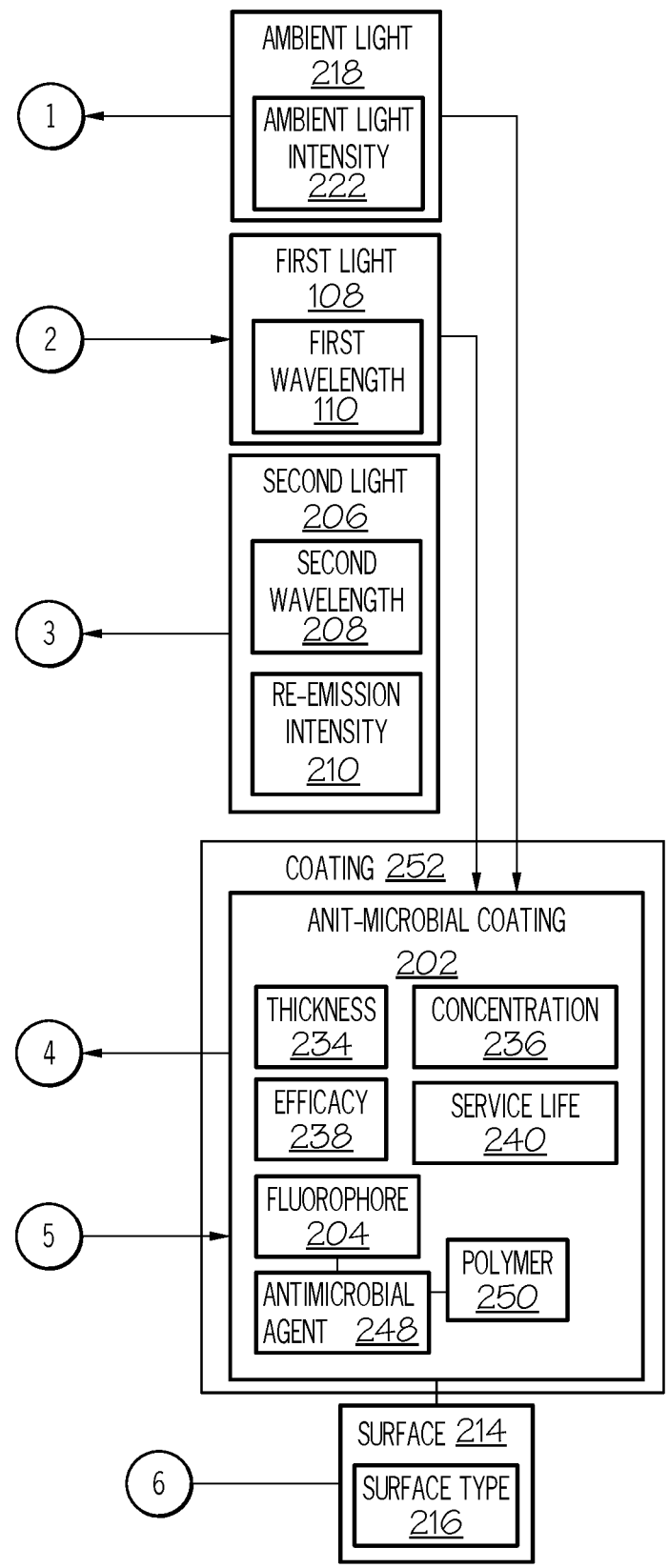
Figure 4:
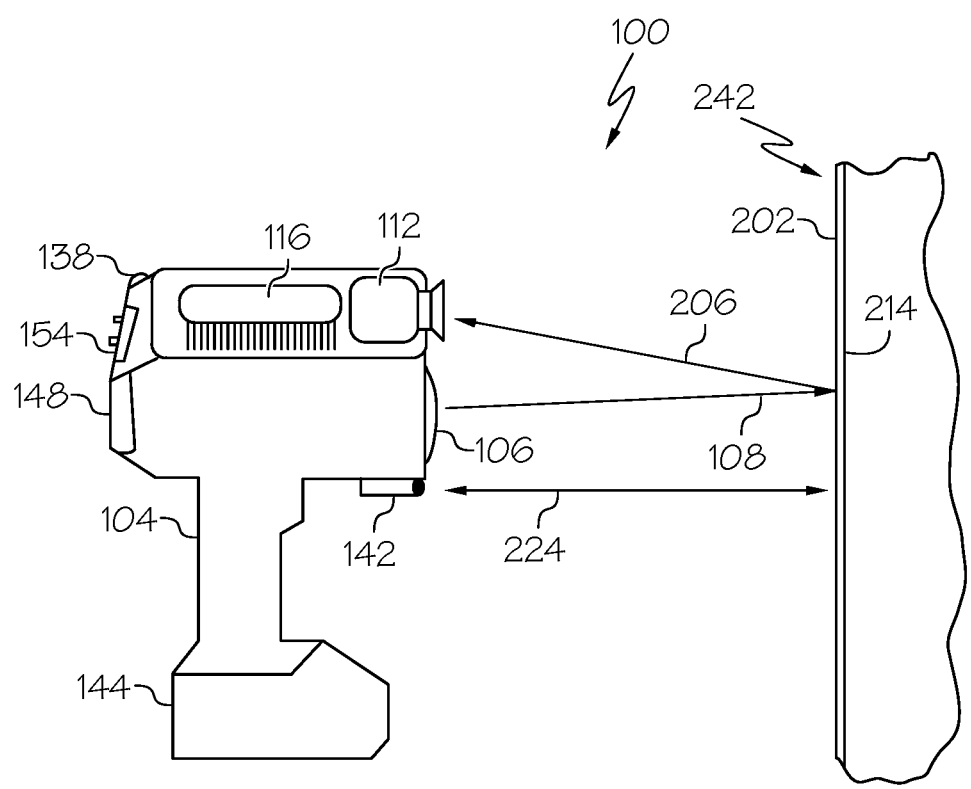
FIG. 4 is a schematic illustration of an example of the device, shown in FIG. 1.

Referring now to FIGS. 1A, 1B and 4, in one or more examples, the device 100 includes a portable housing 104, a light source 106, a light detector 112, and a processing unit 114. Generally, the light source 106, the light detector 112, and the processing unit 114 are coupled to or are otherwise housed by the portable housing 104. The operational and/or functional components of the device 100 being coupled to or disposed within the portable housing 104 integrates such components into a compact unit that can be easily transported to an inspection location and manually operated by a user.

During inspection of the surface 214 and detection of the antimicrobial coating 202, the portable housing 104 enables the light source 106 and the light detector 112 to be positioned relative to the surface 214 upon which the antimicrobial coating 202 is applied. The light source 106 is positioned to direct the first light 108, which may also be referred to as exciting light, onto the surface 214, thereby injecting the first light 108 into the antimicrobial coating 202, which is absorbed by the fluorophore 204 of the antimicrobial coating 202. The light detector 112 is positioned to detect the second light 206, which may also be referred to as fluorescent light, emitted from the fluorophore 204.

In one or more examples, the light source 106 is disposed within the portable housing 104. In one or more examples, the light detector 112 is disposed within the portable housing 104. In one or more examples, the processing unit 114 is disposed within the portable housing 104. For the purpose of the present disclosure, the phrase "disposed within the portable housing," such as in reference to an operational component of the device 100 being disposed within the portable housing 104, refers to at least a portion of the operational component being situated in an interior of the portable housing or being otherwise surrounded by the portable housing. In some examples, a portion of the operational component may extend through the portable housing or be otherwise exposed for operational functions or for interaction with the environment or the user.

In one or more examples, the light source 106 emits (e.g., is configured or adapted to emit) the first light 108. The light source 106 may be or include any suitable device or mechanism capable of generating and emitting the first light 108 for exciting the fluorophore 204 of the antimicrobial coating 202. Suitable light sources provide excitation energy at a wavelength and intensity sufficient to effect fluorescent re-emission from the fluorophore 204 of the antimicrobial coating 202. In one or more examples, the light source 106 provides relatively broad wavelength band excitation (e.g., ultraviolet light source or white light source). In one or more examples, the light source 106 provides relatively narrower wavelength band excitation (e.g., laser or light-emitting diode). Examples of suitable light sources include, but are not limited to, tungsten lamps, halogen lamps, xenon lamps, arc lamps, light-emitting diodes (LEDs), hollow cathode lamps, lasers, and the like.

In one or more examples, the device 100 also includes one or more optical mechanisms to enhance excitation efficiency and/or to select wavelength band excitation. Examples of such optical mechanisms include, but are not limited to, optics, collimating lenses, focusing lenses, waveguides, diffraction gratings, monochromators, and/or filters that suit the fluorophore 204 of the antimicrobial coating 202.

Generally, the first light 108 has the first wavelength 110. In one or more examples, the first light 108 is ultraviolet light. However, in other examples, the first light 108 may be other suitable types of light or electromagnetic radiation. In one or more examples, the first wavelength 110 is in a range of approximately 10 nm to approximately 400 nm. However, in other examples, the first wavelength 110 may have another suitable wavelength or range of wavelengths.

Generally, the second light 206 has the second wavelength 208. In one or more examples, the second light 206 is visible light. In one or more examples, the second light 206 is blue light. However, in other examples, the second light 206 may be other suitable types of light (e.g., other colors of visible light) or detectable electromagnetic radiation. In one or more examples, the second wavelength 208 is in a range of approximately 450 nm to approximately 500 nm. However, in other examples, the second wavelength 208 may have another suitable wavelength or range of wavelengths. The type of the second light 206 and/or the second wavelength 208 is dependent on the type of the fluorophore 204 selected for the antimicrobial coating 202.

In one or more examples, the light detector 112 receives (e.g., is configured or adapted to receive) the second light 206 that is re-emitted from the antimicrobial coating 202. The light detector 112 may be or include any suitable device or mechanism capable of detecting fluorescent emission over the emission wavelength band of the fluorophore 204 of the antimicrobial coating 202. In one or more examples, the light detector 112 is configured or adapted to detect the intensity of the second light 206, referred to herein as re-emission intensity 210. Examples of suitable light detectors include, but are not limited to, cameras, photomultiplier tubes, solid-state detectors, such as photodiodes, optical light sensors, and the like, which are responsive to the wavelength emission band of the fluorophore 204.

In one or more examples, the device 100 includes an optical filter 146. In one or more examples, the optical filter 146 is coupled to or is otherwise disposed within the portable housing 104. The optical filter 146 transmits (e.g., is configured or adapted to transmit) only the second light 206 at the second wavelength 208 to the light detector 112. For example, the optical filter 146 is positioned between the light detector 112 and the surface 214 with the antimicrobial coating 202 that is being tested such that the second light 206 passes through the optical filter 146 before being received and detected by the light detector 112. In one or more examples, the optical filter 146 includes an optical bandpass filter that passes the second wavelength 208 while blocking other wavelengths. As such, the optical filter 146 filters out light having wavelengths that are different than the second wavelength 208 to improve detection and measurement of the re-emission intensity 210 of the second light 206.

In one or more examples, the processing unit 114 is operatively coupled to (e.g., is in communication with) the light detector 112. The processing unit 114 detects and processes (e.g., is configured or adapted to detect and process) the re-emission intensity 210 of the second light 206. Generally, the re-emission intensity and the wavelength (or wavelength distribution) of light re-emitted from various types of fluorophores are well characterized under given conditions. As such, under given conditions, the re-emission intensity 210 and the second wavelength 208 (or wavelength distribution) of the second light 206 re-emitted by the fluorophore 204 selected for the antimicrobial coating 202 will have expected values. Accordingly, the processing unit 114 detects the re-emission intensity 210 and processes the re-emission intensity 210 to determine a value that represents the re-emission intensity 210. In one or more examples, the processing unit 114 determines a value for the re-emission intensity 210 from an input signal or other information or data provided from the light detector 112. The processing unit 114 also determines (e.g., is configured or adapted to determine) a coverage metric 212 of the antimicrobial coating 202 based on the re-emission intensity 210 of the second light 206.

The present disclosure recognizes that, in some instances, a response from the fluorophore 204, such as the re-emission intensity 210 of the second light 206, may be dependent upon various conditions, such as an emission intensity of the first light 108, a distance between the light source 106 and/or the light detector 112 and the surface 214, the type of the surface 214, and ambient light conditions. As such, as will be described in more detail herein, in one or more examples, the device 100 includes or otherwise incorporates a combination of sensors (e.g., distance sensor, ambient light sensor, emission intensity light sensor, camera, and the like.) and dedicated processors (e.g., image processor, illumination processor, and the like.) that are configured to account for these conditions.

Generally, the coverage metric 212 includes any suitable quantifiable or qualifiable characteristic of the antimicrobial coating 202. For example, the coverage metric 212 provides a standard of measurement for the antimicrobial coating 202. The coverage metric 212 of the antimicrobial coating 202 is correlated to or is otherwise associated with the re-emission intensity 210 of the second light 206 emitted by the fluorophore 204 of the antimicrobial coating 202. As such, the processing unit 114 is configured or adapted to select, calculate, or estimate a value for the coverage metric 212 based on a detected value of the re-emission intensity 210 and correlation of the re-emission intensity 210 to the coverage metric 212.

Referring to FIGS. 1A and 1B, in one or more examples, the processing unit 114 includes a data processor 122 and a memory 124 that is coupled to the data processor 122. The memory 124 stores correlation data 126. The correlation data 126 includes a plurality of reference coverage metrics 130 and a plurality of reference re-emission intensities 128 that correspond to the plurality of reference coverage metrics 130. The data processor 122 correlates the value of the re-emission intensity 210 of the second light 206 to the value of one of the plurality of reference coverage metrics 130 to determine the coverage metric 212 of the antimicrobial coating 202.

Figure 5:
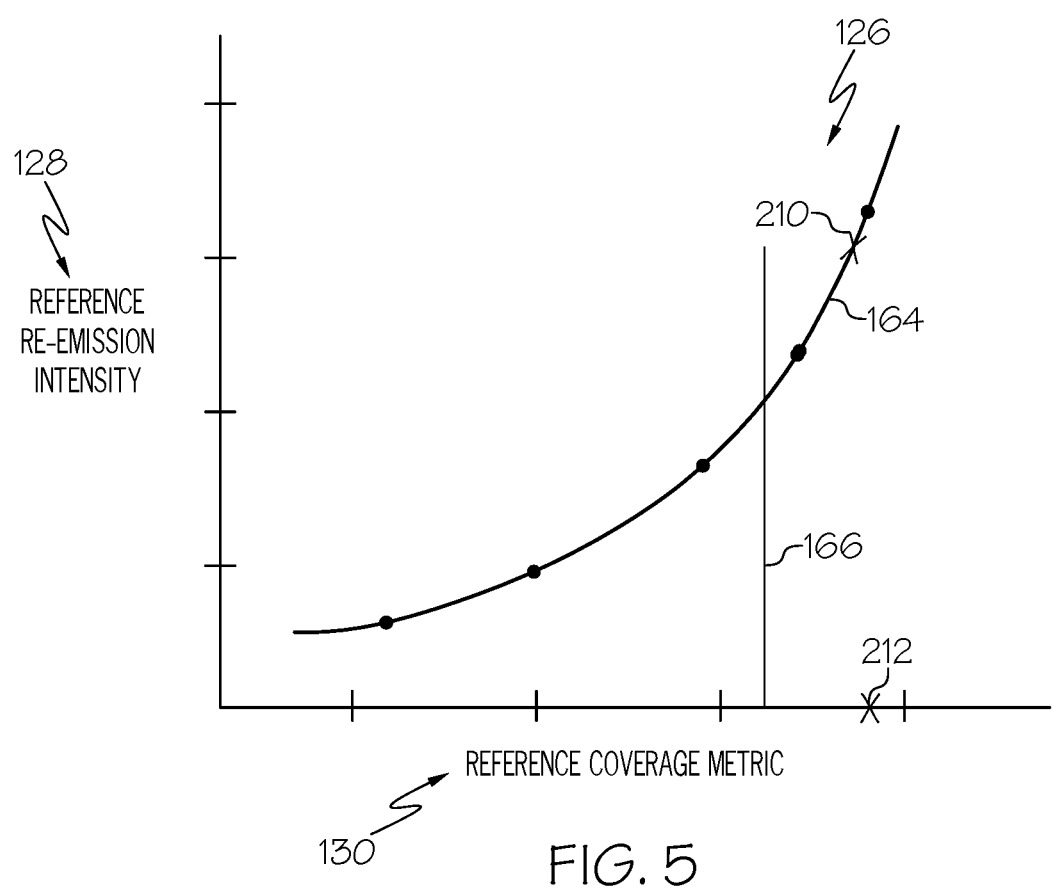
FIG. 5 is a graphical representation of correlation data that includes reference re-emission intensities correlated to reference coverage metrics.

In one or more examples, correlation of the plurality of reference coverage metrics 130 and the plurality of reference re-emission intensities 128 and, thus, generation of the correlation data 126 is performed in a controlled setting. For example, a plurality of test substrates is provided. Each one of the test substrates includes a test surface onto which the antimicrobial coating 202 is applied. The antimicrobial coating 202 of each test substrate includes the reference coverage metric 130 that is unique and that has a known or controlled value. The first light 108 is directed onto the test surface to excite the fluorophore 204 of the antimicrobial coating 202. The reference re-emission intensity 128 of the second light 206, re-emitted by the fluorophore 204 of the antimicrobial coating 202, is measured. The value of the reference re-emission intensity 128 is associated with the value of the reference coverage metric 130. This process is repeated for each one of the plurality of test substrates to generate the plurality of reference coverage metrics 130 and the plurality of reference re-emission intensities 128. The correlation data 126 correlates the value of each one of the plurality of reference coverage metrics 130 to the value of an associated one of the plurality of reference re-emission intensities 128. In one or more examples, the correlation data 126 takes the form of a lookup table, for example, stored on the memory 124 of the processing unit 114. In one or more examples, the correlation data 126 takes the form of a correlation curve 164 (e.g., as shown in FIG. 5). In other examples, correlation of the plurality of reference coverage metrics 130 and the plurality of reference re-emission intensities 128 (e.g., the correlation data 126) may be achieved using other methodologies, such as artificial intelligence, Bayesian statistics, and the like.

FIG. 5 illustrates an example of the correlation curve 164, generated by the correlation data 126. As illustrated, the correlation curve 164 includes or represents the relationship between the measured values of the plurality of reference re-emission intensities 128 and the controlled values for the plurality of reference coverage metrics 130. The correlation curve 164 also provides an estimate for values of the reference coverage metrics 130 and values of the reference re-emission intensities 128 that were not explicitly measured or tested in the control environment.

During inspection of the surface 214 and detection of the antimicrobial coating 202 on the surface 214, the processing unit 114 utilizes the correlation data 126 (e.g., the correlation curve 164) to calculate or estimate the coverage metric 212 based on the re-emission intensity 210 that is detected by the light detector 112 and/or determined by the processing unit 114.

In one or more examples, the coverage metric 212 is a thickness of the antimicrobial coating 202, for example, per unit of area of the surface 214, referred to herein as thickness 234. In one or more examples, the thickness 234 of the antimicrobial coating 202, applied to the surface 214, is compared to a threshold thickness (e.g., approximately known within a specified tolerance). At the threshold thickness of the antimicrobial coating 202, the fluorophore 204 re-emits the second light 206 having a threshold re-emission intensity that is detectable by the device 100. In other words, when the thickness 234 is equal to or greater than the threshold thickness, the re-emission intensity 210 of the second light 206 is sufficient for detection by the device 100, which infers that the surface 214 is sufficiently covered by the antimicrobial coating 202 and that the antimicrobial coating 202 has a sufficient efficacy. In one or more examples, the thickness 234 of the antimicrobial coating 202, as applied, has a known or expected value (e.g., within a specified tolerance) that is represented by the value of one of the plurality of reference coverage metrics 130 (e.g., one of a plurality of reference thicknesses). At each one of the reference thicknesses of the antimicrobial coating 202, the fluorophore 204 re-emits the second light 206 at a value that is represented by a corresponding one of the plurality of reference re-emission intensities 128. Over time and/or due to wear, the thickness 234 of the antimicrobial coating 202 may decrease. A decrease in the thickness 234 of the antimicrobial coating 202 may result in an associated decrease in the amount of fluorophore 204 and, thus, a decrease in the re-emission intensity 210 of the second light 206 emitted by the fluorophore 204 of the antimicrobial coating 202 after excitation by the first light 108. Similarly, a decrease in thickness 234 of the antimicrobial coating 202 may result in or infer an associated decrease in the amount of the antimicrobial agent 248 and, thus, a decrease in the effectiveness of the antimicrobial coating 202. As such, the device 100 provides a measurement or estimate of the thickness 234 of the antimicrobial coating 202 based on the re-emission intensity 210 of the second light 206 emitted by the fluorophore 204 of the antimicrobial coating 202 after excitation by the first light 108. In these examples, the thickness 234 of the antimicrobial coating 202 is representative of the expected effectiveness of the antimicrobial coating 202.

In one or more examples, the coverage metric 212 is a concentration of the antimicrobial coating 202, for example, per unit of area of the surface 214, referred to herein as concentration 236. In one or more examples, the concentration 236 of the antimicrobial coating 202, applied to the surface 214, is compared to a threshold concentration (e.g., approximately known within a specified tolerance). At the threshold concentration of the antimicrobial coating 202, the fluorophore 204 re-emits the second light 206 having a threshold re-emission intensity that is detectable by the device 100. In other words, when the concentration 236 is equal to or greater than the threshold concentration, the re-emission intensity 210 of the second light 206 is sufficient for detection by the device 100, which infers that the surface 214 is sufficiently covered by the antimicrobial coating 202 and that the antimicrobial coating 202 has a sufficient efficacy. In one or more examples, the concentration 236 of the antimicrobial coating 202, as applied, has a known or expected value (e.g., within a specified tolerance) that is represented by the value of one of the plurality of reference coverage metrics 130 (e.g., one of a plurality of reference concentrations). At each one of the reference concentrations of the antimicrobial coating 202, the fluorophore 204 re-emits the second light 206 at a value that is represented by a corresponding one of the plurality of reference re-emission intensities 128. Over time and/or due to wear, the concentration 236 of the antimicrobial coating 202 may decrease. A decrease in the concentration 236 of the antimicrobial coating 202 may result in an associated decrease in the amount of fluorophore 204 and, thus, a decrease in the re-emission intensity 210 of the second light 206 emitted by the fluorophore 204 of the antimicrobial coating 202 after excitation by the first light 108. Similarly, a decrease in concentration 236 of the antimicrobial coating 202 may result in or infer an associated decrease in the amount of the antimicrobial agent 248 and, thus, a decrease in the effectiveness of the antimicrobial coating 202. As such, the device 100 provides a measurement or estimate of the concentration 236 of the antimicrobial coating 202 based on the re-emission intensity 210 of the second light 206 emitted by the fluorophore 204 of the antimicrobial coating 202 after excitation by the first light 108. In these examples, the concentration 236 of the antimicrobial coating 202 is representative of the expected effectiveness of the antimicrobial coating 202.

In one or more examples, the coverage metric 212 is an efficacy of the antimicrobial coating 202, referred to herein as efficacy 238. The efficacy 238 of the antimicrobial coating 202 refers to the degree to which the antimicrobial coating 202 hinders or stops the growth of disease-causing micro-organisms. In one or more examples, the efficacy 238 of the antimicrobial coating 202, applied to the surface 214, is compared to a threshold efficacy (e.g., approximately known within a specified tolerance). At the threshold efficacy of the antimicrobial coating 202, the fluorophore 204 re-emits the second light 206 having a threshold re-emission intensity that is detectable by the device 100. In other words, when the efficacy 238 is equal to or greater than the threshold efficacy, the re-emission intensity 210 of the second light 206 is sufficient for detection by the device 100, which infers that the surface 214 is sufficiently covered by the antimicrobial coating 202 and that the antimicrobial coating 202 has a sufficient efficacy. In one or more examples, the efficacy 238 of the antimicrobial coating 202, as applied, has a known or expected value (e.g., within a specified tolerance) that is represented by the value of one of the plurality of reference coverage metrics 130 (e.g., one of a plurality of reference efficacies). At each one of the reference efficacies of the antimicrobial coating 202, the fluorophore 204 re-emits the second light 206 at a value that is represented by a corresponding one of the plurality of reference re-emission intensities 128. Over time and/or due to wear, the efficacy 238 of the antimicrobial coating 202 may decrease. In one or more examples, the efficacy 238 of the antimicrobial coating 202 is related to or can be estimated as a function of the thickness 234 and/or the concentration 236 of the antimicrobial coating 202. Thus, a decrease in the thickness 234 and/or a decrease in the concentration 236 of the antimicrobial coating 202 may indicate an associated decrease in the efficacy 238 of the antimicrobial coating 202. As an example, a value for a reference efficacy may be measured or otherwise tested for each one of a plurality of reference thicknesses of the antimicrobial coating 202, which is then correlated to the value of an associated one of the plurality of reference re-emission intensities 128. As another example, a value for the reference efficacy may be measured or otherwise tested for each one of a plurality of reference concentrations of the antimicrobial coating 202, which is then correlated to the value of an associated one of the plurality of reference re-emission intensities 128. As such, the device 100 provides a measurement or estimate of the efficacy 238 of the antimicrobial coating 202 based on the re-emission intensity 210 of the second light 206 emitted by the fluorophore 204 of the antimicrobial coating 202 after excitation by the first light 108.

In one or more examples, the coverage metric 212 is a service life expectancy of the antimicrobial coating 202, referred to herein as service life 240. The service life 240 of the antimicrobial coating 202 refers to the time during which the antimicrobial coating 202 is expected to remain effective against disease-causing micro-organisms. In one or more examples, the service life 240 of the antimicrobial coating 202, applied to the surface 214, is compared to a threshold service life (e.g., approximately known within a specified tolerance). At the threshold service life of the antimicrobial coating 202, the fluorophore 204 re-emits the second light 206 having a threshold re-emission intensity that is detectable by the device 100. In other words, when the service life 240 is equal to or greater than the threshold service life, the re-emission intensity 210 of the second light 206 is sufficient for detection by the device 100, which infers that the surface 214 is sufficiently covered by the antimicrobial coating 202 and that the antimicrobial coating 202 has a sufficient efficacy. In one or more examples, the service life 240 of the antimicrobial coating 202, as applied, has a known or expected value (e.g., within a specified tolerance) that is represented by the value of one of the plurality of reference coverage metrics 130 (e.g., one of a plurality of reference service lives). At each one of the reference service lives of the antimicrobial coating 202, the fluorophore 204 re-emits the second light 206 at a value that is represented by a corresponding one of the plurality of reference re-emission intensities 128. Over time and/or due to wear, the service life 240 of the antimicrobial coating 202 decreases. In one or more examples, the service life 240 of the antimicrobial coating 202 is related to or can be estimated as a function of the thickness 234 and/or the concentration 236 of the antimicrobial coating 202. Thus, a decrease in the thickness 234 and/or a decrease in the concentration 236 of the antimicrobial coating 202 may indicate an associated decrease in the service life 240 of the antimicrobial coating 202. As an example, a value for a reference service life may be estimated or otherwise tested for each one of a plurality of reference thicknesses of the antimicrobial coating 202, which is then correlated to the value of an associated one of the plurality of reference re-emission intensities 128. As another example, a value for the reference service life may be estimated or otherwise tested for each one of a plurality of reference concentrations of the antimicrobial coating 202, which is then correlated to the value of an associated one of the plurality of reference re-emission intensities 128. As such, the device 100 provides a measurement or estimate of the service life 240 (e.g., remaining service life) of the antimicrobial coating 202 based on the re-emission intensity 210 of the second light 206 emitted by the fluorophore 204 of the antimicrobial coating 202 after excitation by the first light 108.

Referring again to FIGS. 1A and 1B, in one or more examples, the light detector 112 includes or takes the form of a camera 116. The camera 116 captures (e.g., is configured or adapted to capture) an illuminated image 118 of the surface 214 on which the antimicrobial coating 202 is applied and that is illuminated by the first light 108.

For the purpose of the present disclosure, the term "illuminated image," such as in reference to the illuminated image 118, refers to an image of a surface that is coated with the antimicrobial coating 202 and that is illuminated by exciting light (e.g., the first light 108). As such, the illuminated image 118 may also be referred to as an excited image. For the purpose of the present disclosure, an item, such as a surface, being illuminated by excitation light refers to the item, such as the surface, having the exciting light (e.g., the first light 108) directed or shined onto at least a portion of the item, such as at least a portion of the surface.

The camera 116 includes any suitable optical instrument that captures a visual image. In one or more examples, the camera 116 captures a single image. In one or more examples, the camera 116 captures a series of images in sequence at a specified frame rate (e.g., video). In one or more examples, the camera 116 is a digital camera or digital video recorder that generates a digital image (e.g., the illuminated image 118 is a digital image). The illuminated image 118 (e.g., digital image) includes pixels. Each one of the pixels includes discrete quantities of numeric representation for its intensity and color.

In one or more examples, the camera 116 includes a bandpass lens 152. The bandpass lens 152 transmits (e.g., is configured or adapted to transmit) only the second light 206 at the second wavelength 208. The bandpass lens 152 is an example of the optical filter 146.

In one or more examples, the processing unit 114 includes an image processor 120. The image processor 120 analyzes (e.g., is configured or adapted to analyze) the illuminated image 118 and calculates or otherwise determines the re-emission intensity 210 of the second light 206 represented in the illuminated image 118. In other words, the image processor 120 quantifies (e.g., within a specified tolerance) the intensity of the second light 206 from the illuminated image 118.

In one or more examples, the image processor 120 recognizes and locates one or more regions of the illuminated image 118 that represent the second light 206. For example, the image processor 120 identifies pixels in the illuminated image 118 that have a color (e.g., a color value) that matches the second light 206 (e.g., blue pixels represent the blue light emitted from the fluorophore 204 of the antimicrobial coating 202). The image processor 120 analyzes the color and intensity of the pixels and generates an output as a value for the intensity of the light represented by the pixels. This value is used for the re-emission intensity 210 of the second light 206.

In one or more examples, the image processor 120 additionally pre-processes and/or post-processes the illuminated image 118. Pre-processing and/or post-processing of the illuminated image 118 is adapted to enhance and/or normalize the illuminated image 118. In one or more examples, the pre-processing and/or post-processing may include the use of information or other data generated from the sensors (e.g., distance sensor, ambient light sensor, emission intensity light sensor, etc.) of the device 100.

In other examples, the light detector 112 includes or takes the form of an array of photodiodes. The array of photodiodes is configured to be excited only by the re-emitted wavelength (e.g., the second wavelength 208) of the second light 206. Use of the array of photodiodes would advantageously reduce the computational load on the processing unit 114.

In other examples, the device 100 uses data processing techniques, such as computer vision, artificial intelligence, Bayesian statistics, etc. to detect the re-emission intensity 210 of the second light 206. These techniques may beneficially improve the accuracy of detection of the re-emitted light and the coverage assessment.

The present disclosure recognizes that, in some instances, the re-emission intensity 210 of the second light 206 re-emitted from the antimicrobial coating 202 may depend on or be a function of the type or physical characteristics of the surface 214, referred to herein as surface type 216, upon which the antimicrobial coating 202 is applied. As an example, the re-emission intensity 210 of the second light 206 may differ for a given coverage metric 212 (e.g., thickness 234, concentration 236, efficacy 238, service life 240) between a hard, smooth surface; a hard, textured surface, a soft, smooth surface, a soft, textured surface, or other surface types. In one or more examples, the device 100 facilitates compensation for such differences in the surface type 216.

Referring still to FIGS. 1A and 1B, in one or more examples, the memory 124 stores a plurality of reference surface types 134. The memory 124 also stores sets 136 of the correlation data 126. Each one of the sets 136 of the correlation data 126 corresponds to one of the plurality of reference surface types 134. For example, each one of the reference surface types 134 is correlated to or otherwise associated with one of the sets 136. The correlation data 126 of each one of the sets 136, associated with a respective one of the reference surface types 134, includes the plurality of the reference coverage metrics 130 and the correlated plurality of the reference re-emission intensities 128 that corresponds to the respective one of the reference surface types 134. Generation of the plurality of reference surface types 134 and correlation of each one of the plurality of reference surface types 134 to an associated set 136 of the correlation data 126 may be performed in a controlled setting.

Referring to FIGS. 1A, 1B and 4, in one or more examples, the device 100 includes a user interface 154. In one or more examples, the user interface 154 is coupled to or is otherwise disposed within the portable housing 104. The user interface 154 includes or takes the form of any suitable input/output (I/O) unit or point of human-computer interaction and communication with the device 100, such as a touch screen, a keypad, or the like.

In one or more examples, the device 100 facilitates manual selection of the reference surface type 134. In one or more examples, the user interface 154 provides a user-based selection of one of the plurality of reference surface types 134. For example, a user may manually select one of the plurality of reference surface types 134 that best matches the surface type 216 of the surface 214. The data processor 122 selects one of the sets 136 of the correlation data 126 based on the user-based selection of one of the plurality of reference surface types 134.

In one or more examples, the device 100 facilitates or is operable to automatically select the reference surface type 134. In one or more examples, the camera 116 captures an unilluminated image 132 of the surface 214 on which the antimicrobial coating 202 is applied and that is not illuminated by the first light 108.

For the purpose of the present disclosure, the term "unilluminated image," such as in reference to the unilluminated image 132, refers to an image of a surface that is coated with the antimicrobial coating 202 and that is not illuminated by exciting light (e.g., the first light 108). As such, the unilluminated image 132 may also be referred to as an unexcited image. For the purpose of the present disclosure, an item, such as a surface, being unilluminated by the exciting light refers to the item, such as the surface, not having the exciting light (e.g., the first light 108) directed or shined onto at least a portion of the item, such as at least a portion of the surface. An item, such as a surface, being unilluminated by the exciting light does not exclude instances in which the item, such as the surface, is illuminated by ambient light 218.

In these examples, the unilluminated image 132 serves as, and may also be referred to as, a reference image that is used by the processing unit 114 to determine an appropriate one of the plurality of reference surface types 134 that best matches the surface type 216 of the surface 214. In one or more examples, the image processor 120 analyzes the unilluminated image 132 to determine the surface type 216 of the surface 214. For example, the image processor 120 processes and analyzes the unilluminated image 132 and extracts information from the image that is representative of the surface type 216 (e.g., reflectivity, surface texture, etc.).

In one or more examples, the data processor 122 selects one of the sets 136 of the correlation data 126 based on the surface type 216. For example, the data processor 122 selects one of the plurality of reference surface types 134 that best represents the surface type 216 and selects a corresponding one of the sets 136 of the correlation data 126 that is associated with the selected one of the plurality of reference surface types 134.

The present disclosure recognizes that, in some instances, determination of the re-emission intensity 210 of the second light 206 re-emitted from the antimicrobial coating 202 may be obscured by ambient light 218. As an example, in ambient light situations, the light received and detected by the light detector 112 may include the second light 206 and a portion of the ambient light 218 having a wavelength that is equal (e.g., approximately equal) to the second wavelength 208 of the second light 206. For example, during an inspection operation, the light detector 112 may receive and detect the blue light re-emitted from the fluorophore 204 of the antimicrobial coating 202 and the blue-light portion of the ambient light 218. In one or more examples, the device 100 facilitates compensation for the ambient light 218.

Referring to FIGS. 1A, 1B and 4, in one or more examples, the device 100 includes an ambient light sensor 138. In one or more examples, the ambient light sensor 138 is coupled to or is otherwise disposed within the portable housing 104. The ambient light sensor 138 includes or takes the form of any suitable device that converts light energy into an electrical signal output that is processed by the processing unit 114, such as, but not limited to, photoresistors, photodiodes, phototransistors, and the like.

In one more examples, the ambient light sensor 138 detects (e.g., is configured or adapted to detect) ambient light 218. In an example, the device 100 may provide an indication (e.g., visual and/or audible via a display 148) to the user that there is an ambient light condition or that the ambient light 218 surrounding the device 100 and/or the surface 214 surpasses a predetermined threshold in which accurate determination of the re-emission intensity 210 of the second light 206 may be affected. In one or more examples, a signal from the ambient light sensor 138 is used by the processing unit 114 to automatically adjust the coverage analysis to account for the ambient light 218 such that the detecting and processing operations are invariant to the ambient light 218.

In one or more examples, the camera 116 captures the unilluminated image 132 of the surface 214 on which the antimicrobial coating 202 is applied and that is not illuminated by the first light 108. In these examples, the unilluminated image 132 serves as, and may also be referred to as, a reference image that is used by the processing unit 114 to determine an ambient light intensity 222 of the ambient light 218. In one or more examples, the image processor 120 analyzes the unilluminated image 132 to calculate the ambient light intensity 222 of the ambient light 218.

In one or more examples, the memory 124 stores a plurality of reference ambient light intensities 156. The memory 124 also stores the sets 136 of the correlation data 126. Each one of the sets 136 of the correlation data 126 corresponds to one of the plurality of reference ambient light intensities 156. For example, each one of the reference ambient light intensities 156 is correlated to or otherwise associated with one of the sets 136. The correlation data 126 of each one of the sets 136, associated with a respective one of the reference ambient light intensities 156, includes the plurality of the reference coverage metrics 130 and the correlated plurality of the reference re-emission intensities 128 that corresponds to the respective one of the plurality of reference ambient light intensities 156. Generation of the plurality of reference ambient light intensities 156 and correlation of each one of the plurality of reference ambient light intensities 156 to an associated set 136 of the correlation data 126 may be performed in a controlled setting.

In one or more examples, the data processor 122 selects one of the sets 136 of the correlation data 126 based on the ambient light intensity 222. For example, the data processor 122 selects one of the plurality of reference ambient light intensities 156 that best represents the ambient light intensity 222 of the ambient light 218 and selects a corresponding one of the sets 136 of the correlation data 126 that is associated with the selected one of the plurality of reference ambient light intensities 156.

In one or more examples, the processing unit 114 is configured or adapted to perform an analytical or computational analysis that compensates the value for the re-emission intensity 210 of the second light 206 for the value of the ambient light intensity 222 of the ambient light 218, for example, determined by the image processor 120, from the unilluminated image 132. For example, the image processor 120 analyzes the unilluminated image 132 to determine the ambient light intensity 222 of ambient light 218 received by the light detector 112. In one or more examples, the device 100 (e.g., the processing unit 114) includes an illumination processor 140. In one or more examples, the processing unit 114 (e.g., the illumination processor 140) compensates the re-emission intensity 210 of the second light 206 for the ambient light intensity 222. For example, the illumination processor 140 cancels a portion of the value for the re-emission intensity 210 of the second light 206 represented by the value of the ambient light intensity 222 of the ambient light 218 or otherwise reduces the value for the re-emission intensity 210 of the second light 206 by the value of the ambient light intensity 222 of the ambient light 218.

In one or more examples, the processing unit 114 is operatively coupled to the ambient light sensor 138. The device 100 (e.g., the processing unit 114) includes the illumination processor 140. The illumination processor 140 calculates (e.g., is configured or adapted to calculate) the ambient light intensity 222 of the ambient light 218, for example, based on the electrical signal provided by the ambient light sensor 138 (e.g., without capturing and analyzing the unilluminated image 132). The illumination processor 140 compensates (e.g., is configured or adapted to compensate) the re-emission intensity 210 of the second light 206 for the ambient light intensity 222 of the ambient light 218.

The present disclosure recognizes that, in some instances, accurate and consistent determination of the re-emission intensity 210 of the second light 206 re-emitted from the antimicrobial coating 202 may depend on a distance between the device 100 and the surface 214, such as a distance between the light source 106 and/or the light detector 112 and the surface 214, and/or on a contour, geometry, or shape of the surface 214, referred to herein as distance 224. As an example, the re-emission intensity 210 of the second light 206 may differ for a given coverage metric 212 (e.g., thickness 234, concentration 236, efficacy 238, service life 240) at different distances between the device 100 and the surface 214. As another example, the re-emission intensity 210 of the second light 206 may differ for a given coverage metric 212 (e.g., thickness 234, concentration 236, efficacy 238, service life 240) at different regions of the surface 214 having a relatively more complex shape (e.g., not straight or flat). In one or more examples, the device 100 facilitates compensation for such differences the distance 224.

Referring to FIGS. 1A, 1B and 4, in one or more examples, the device 100 includes a distance measurer 142. In one or more examples, the distance measurer 142 is coupled to or is otherwise disposed within the portable housing 104. The distance measurer 142 includes or takes the form of any suitable device or sensor that measures the distance between two points, such as, but not limited to, an ultrasonic distance sensor, an infrared distance sensor, a laser distance sensor, a depth sensor, a depth camera, a machine vision system, and the like.

In one or more examples, the distance measurer 142 calculates (e.g., is configured or adapted to calculate) the distance 224 between the device 100 (e.g., the light source 106 and/or the light detector 112) and the surface 214. In an example, the device 100 may provide an indication (e.g., visual or audible via the display 148) to the user of the distance 224. In another example, additionally or alternatively, the device 100 may provide an indication (e.g., visual or audible via the display 148) to the user that the distance 224 is outside of a predetermined threshold in which accurate determination of the re-emission intensity 210 of the second light 206 may be affected. In this example, the user may adjust the distance 224 as needed to obtain or maintain the distance 224 that is desired or appropriate for inspection of the antimicrobial coating 202.

In one or more examples, the distance measurer 142 is operatively coupled to the processing unit 114. The memory 124 stores a plurality of reference distances 158. The memory 124 also stores the sets 136 of the correlation data 126. Each one of the sets 136 of the correlation data 126 corresponds to one of the plurality of reference distances 158. For example, each one of the reference distances 158 is correlated to or otherwise associated with one of the sets 136. The correlation data 126 of each one of the sets 136, associated with a respective one of the reference distances 158, includes the plurality of the reference coverage metrics 130 and the correlated plurality of the reference re-emission intensities 128 that corresponds to the respective one of the plurality of reference distances 158. Generation of the plurality of reference distances 158 and correlation of each one of the plurality of reference ambient light intensities 156 to an associated set 136 of the correlation data 126 may be performed in a controlled setting.

In one more examples, the data processor 122 selects one of the sets 136 of the correlation data 126 based on the distance 224. For example, the data processor 122 selects one of the plurality of reference distances 158 that best represents the distance 224 and selects a corresponding one of the sets 136 of the correlation data 126 that is associated with the selected one of the plurality of reference distances 158.

In one or more examples, the distance measurer 142 includes or takes the form of a RGB-D sensor or RGB-D camera. The RGB-D camera includes a depth-sensing device that works in association with a RGB (red, green and blue color) sensor camera. The RGB-D sensor is configured to augment a conventional image with depth information related with the distance to the sensor in a per-pixel basis. In one or more examples, the RGB-D camera generates or provides a 3D point cloud that provides an accurate assessment of the distance 224 and an accurate assessment of the geometry of the surface 214, which may account for non-planar surfaces or complex surface geometries in which different portions of the surface 214 represented in an image are at different distances from the device 100 and beneficially increases the sensitivity and/or accuracy of the coverage assessment.

Referring still to FIGS. 1A, 1B and 4, in one or more examples, the device 100 includes the display 148. The display 148 includes any suitable mechanism to display information to the user, such as a light-emitting diode display, a liquid crystal display, and the like. In one or more examples, the display 148 and the user interface 154 are integrated into a single unit.

In one or more examples, the display 148 provides at least one of a visual representation 150 of the coverage metric 212 and/or an audible indication 160 of the coverage metric 212. As an example, the display 148 provides a qualitative representation of the coverage metric 212 (e.g., thickness 234, concentration 236, efficacy 238, service life 240, and the like) for the antimicrobial coating 202 based on the re-emission intensity 210 of the second light 206 re-emitted by the fluorophore 204 of the antimicrobial coating 202. As another example, the display 148 provides a quantitative representation of the coverage metric 212 (e.g., thickness 234, concentration 236, efficacy 238, service life 240, and the like) for the antimicrobial coating 202 based on the re-emission intensity 210 of the second light 206 re-emitted by the fluorophore 204 of the antimicrobial coating 202.

In one or more examples, the qualitative representation may include a "GO" or "NO GO" or a "PASS" or "FAIL" indication for the antimicrobial coating 202. In these examples, the processing unit 114 may utilize a coverage threshold 166 (e.g., as shown in FIG. 5) that represents the coverage metric 212 being in an approximate minimum allowable condition. When the re-emission intensity 210 is above the coverage threshold 166, the device 100 may provide an indication that the antimicrobial coating 202 is sufficient to be effective. When the re-emission intensity 210 is below the coverage threshold 166, the device 100 may provide an indication that the antimicrobial coating 202 is insufficient to be effective.

In one or more examples, the quantitative representation may include an indication of a value that, at least estimates or approximates, a measurement for coverage metric 212 of the antimicrobial coating 202 (e.g., a thickness estimate, a concentration estimate, an efficacy estimate, a service life estimate). In these examples, the processing unit 114 may utilize the correlation data 126 (e.g., the correlation curve 164) to determine at least an estimated value for the coverage metric 212 based on the re-emission intensity 210 of the second light 206. As an example, a numerical value of the thickness 234, a numerical value of the concentration 236, a numerical value of the service life 240 remaining, or a numerical value (e.g., percentage) of the efficacy 238 may be displayed.

In one or more examples, the device 100 is configured or adapted to provide a recommendation based on the coverage metric 212. For example, the device 100 provides an advisory action 162 to the user (e.g., via the display 148). The advisory action 162 may include any suitable information related to the condition of, service of, or follow-on action for the antimicrobial coating 202. As an example, the advisory action 162 may include an indication that the antimicrobial coating 202 is below an effectiveness threshold (e.g., when the coverage metric 212, such as the thickness 234, concentration 236, or efficacy 238, is below the coverage threshold 166) and a recommendation to reapply the antimicrobial coating 202 on the surface 214. As another example, the advisory action 162 may include an indication that an end of the service life 240 for the antimicrobial coating 202 is approaching and a recommendation that reapplication of the antimicrobial coating 202 be scheduled. In one or more examples, the advisory action 162 may include automatic re-application of the antimicrobial coating 202 (e.g., using a system 200) when the antimicrobial coating 202 is below an effectiveness or efficacy threshold.

In one or more examples, the device 100 includes a power supply 144. In one or more examples, the power supply 144 is coupled to or is otherwise disposed within the portable housing 104. The power supply 144 supplies power to the operational or functional components of the device 100, such as the light source 106, the light detector 112, the processing unit 114, the ambient light sensor 138, the distance measurer 142, the user interface 154, the display 148, and the like.

Referring generally to FIGS. 1A, 1B and 2-6, by way of examples, the present disclosure is also directed to the system 200 for sanitizing the surface 214. Generally, the system 200 facilitates application of the antimicrobial coating 202 on the surface 214 and routine or impromptu inspection of the surface 214 to determine the coverage metric 212 and, optionally, provide the advisory action 162, such as automatic re-application of the antimicrobial coating 202. Optionally, in one or more examples, the system 200 also facilitates utilization of the device 100 to improve detection and measurement of the re-emission intensity 210 of the second light 206 and, thus, determination of the coverage metric 212.

Figure 6:
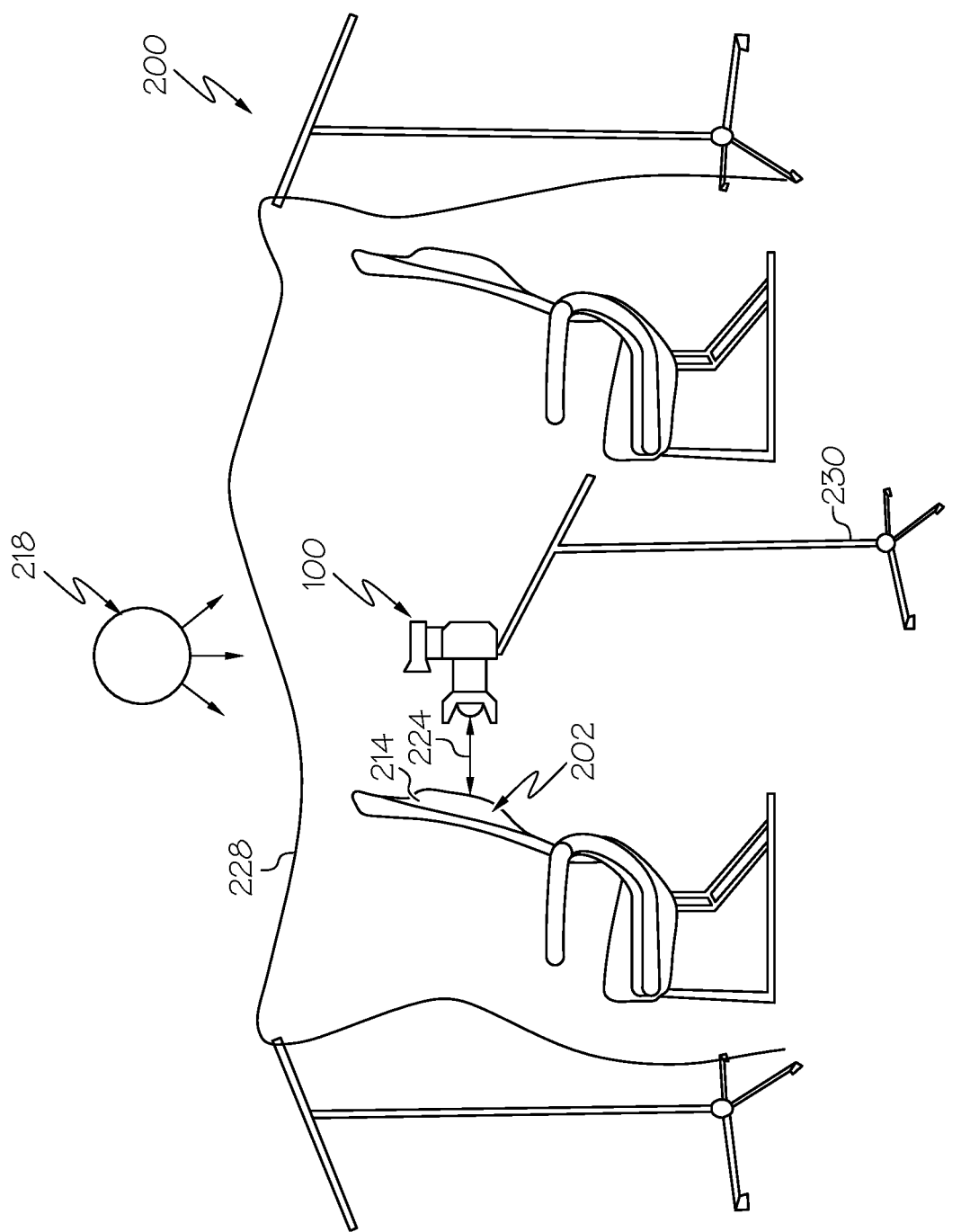
FIG. 6 is a schematic illustration of an example of the system, shown in FIG. 1.

Referring now to FIGS. 1A, 1B and 6, in one or more examples, the system 200 includes the antimicrobial coating 202. The antimicrobial coating 202 is appliable to the surface 214. As described above, the antimicrobial coating 202 includes the fluorophore 204 that, in response to excitation by the first light 108 at the first wavelength 110, re-emits the second light 206 at the second wavelength 208, which is different than the first wavelength 110.

The system 200 includes the device 100 for detecting the antimicrobial coating 202 on the surface 214. The device 100 includes the operational and/or functional components as described in any of the examples provided herein above and illustrated in FIGS. 1-5. The device 100 operates to determine the re-emission intensity 210 of the second light 206 re-emitted by the antimicrobial coating 202 during a surface inspection operation as described in any of the examples provided herein above and illustrated in FIGS. 1-5.

In one or more examples, the device 100 includes the portable housing 104, the light source 106, the light detector 112, and the processing unit 114. As described herein above, in one or more examples, the light source 106 emits the first light 108 at the first wavelength 110. The light detector 112 receives the second light 206 re-emitted from the antimicrobial coating 202. The processing unit 114 is operatively coupled to the light detector 112. The processing unit 114 determines the re-emission intensity 210 of the second light 206 and determines the coverage metric 212 of the antimicrobial coating 202 based on the re-emission intensity 210 of the second light 206.

In one or more examples, the processing unit 114 includes one or more of the image processor 120, the data processor 122, the memory 124, the illumination processor 140, and any other suitable processors and/or storage devices, as described in any of the examples provided herein above. In one or more examples, the device 100 includes other operational and/or functional components, such as the ambient light sensor 138, the distance measurer 142, the display 148, the user interface 154, the power supply 144, and the like, as described in any one of the examples provided herein above.

In one or more examples, the system 200 includes a blackout cover 228. The blackout cover 228 at least partially surrounds (e.g., is configured to at least partially surround) the surface 214. The blackout cover 228 blocks (e.g., is configured to block) substantially all of the ambient light 218. The blackout cover 228 may include or take the form of any suitable covering that provides a dark enclosure within which the surface 214 and the device 100 can be situated, such as a canopy, a curtain, a movable structure, and the like. Utilization of the blackout cover 228 reduces or eliminates the effect of the ambient light 218 on the detection and measurement of the re-emission intensity 210 of the second light 206 and, thus, may improve the accuracy of the detection and measurement of the re-emission intensity 210 of the second light 206.

In one or more examples, the system 200 includes a base 230. The base 230 is configured to support the device 100 during the surface inspection operation. For example, the device 100 is coupled to the base 230. In one or more examples, the device 100 is coupled to the base 230 at a predetermined distance from the surface 214. As such, the distance 224 is selected, obtained, and maintained during the surface inspection operation, which reduces or eliminates the effect of varying distances on the detection and measurement of the re-emission intensity 210 of the second light 206 and, thus, may improve the accuracy of the detection and measurement of the re-emission intensity 210 of the second light 206.

In one or more examples, the system 200 includes an applicator 232. The applicator 232 applies (e.g., is configured or adapted to apply and/or re-apply) the antimicrobial coating 202 to the surface 214. The applicator 232 includes any coating application machine or equipment suitable for applying the antimicrobial coating 202, such as a roller, a sprayer, a brush coater, a wiper, and the like. In one or more examples, the applicator 232 is used to apply an initial coat of the antimicrobial coating 202 on the surface 214. In one or more examples, the applicator 232 is used to re-apply and add subsequent coats of the antimicrobial coating 202, for example, during routine service and maintenance or in response to inspection and the advisory action 162.

Figure 7:
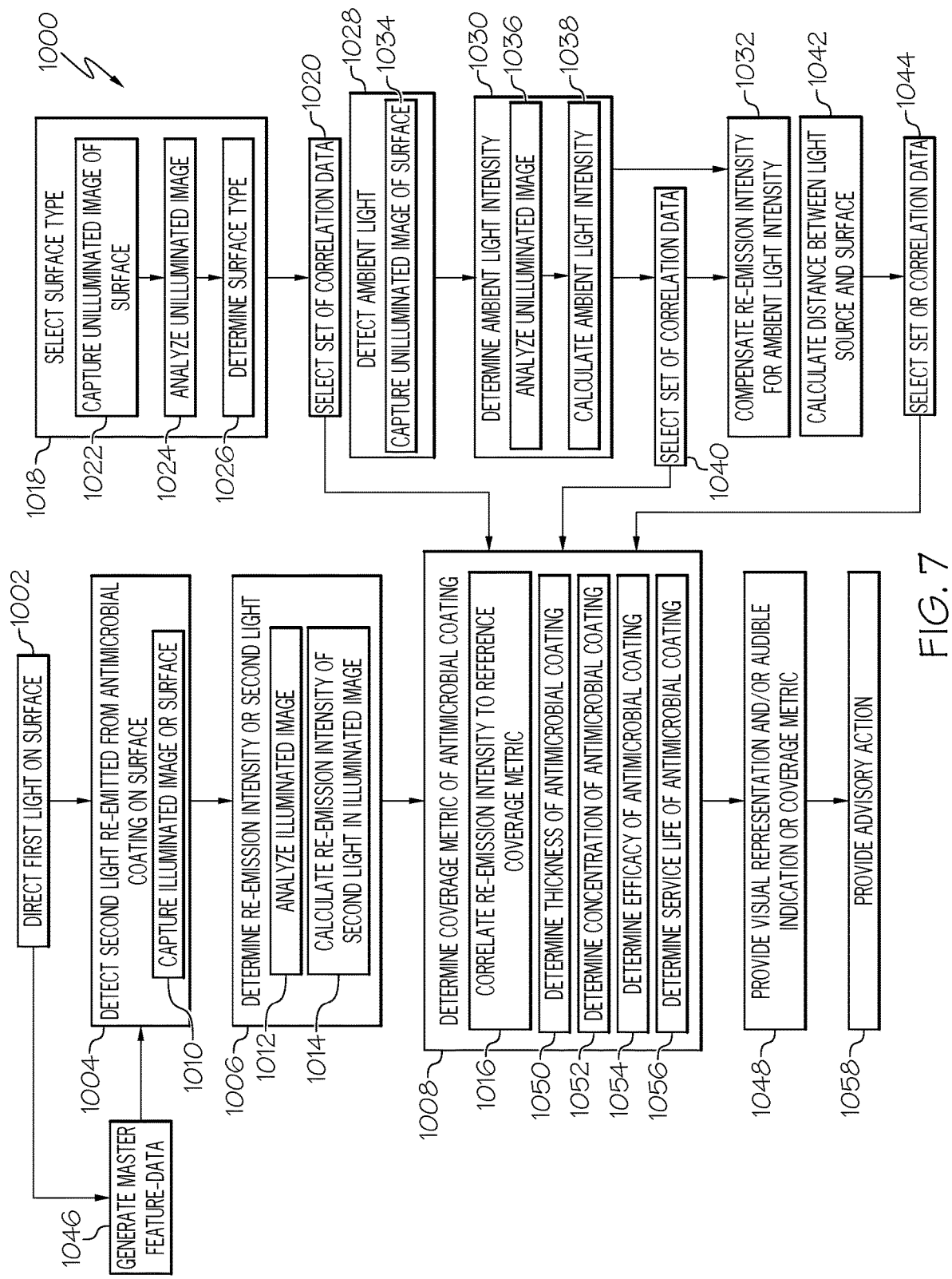
FIG. 7 is a flow diagram of an example of a method for detecting an antimicrobial polymer coating.

Referring now generally to FIGS. 1A, 1B and 2-6 and particularly to FIG. 7, by way of examples, the present disclosure is also directed to a method 1000 for detecting the antimicrobial coating 202 applied to the surface 214. More particularly, the method 1000 is directed to inspecting the surface 214 and determining the coverage metric 212 for the antimicrobial coating 202. In one or more examples, the method 1000 is implemented using the device 100. In one or more examples, the method 1000 is implemented using the system 200.

Referring to FIG. 7, in one or more examples, the method 1000 includes a step of (block 1002) directing the first light 108 having the first wavelength 110 at the surface 214. In one or more examples, according to the method 1000, the step of (block 1002) directing the first light 108 having the first wavelength 110 at the surface 214 is performed using the device 100. For example, the first light 108 is emitted by the light source 106 of the device 100 and is directed onto at least a portion of the surface 214 that is being inspected.

The antimicrobial coating 202 includes the fluorophore 204 that re-emits the second light 206 having the second wavelength 208 in response to excitation by the first light 108. The second wavelength 208 of the second light 206 (e.g., blue light) is different than the first wavelength 110 of the first light 108 (e.g., ultraviolet light).

In one or more examples, according to the method 1000, the step of (block 1002) directing the first light 108 includes a step of directing ultraviolet light, having a wavelength in a range of approximately 10 nm to approximately 400 nm. In one or more examples, the second light 206 is blue light, having a wavelength in a range of approximately 450 nm to approximately 500 nm.

In one or more examples, the method 1000 includes a step of (block 1004) detecting the second light 206 re-emitted from the antimicrobial coating 202. In one or more examples, according to the method 1000, the step of (block 1004) detecting the second light 206 re-emitted from the antimicrobial coating 202 is performed using the device 100. For example, the second light 206 is received by the light detector 112 of the device 100.

In one or more examples, the method 1000 includes a step of (block 1006) detecting, processing, and/or otherwise determining the re-emission intensity 210 of the second light 206. In one or more examples, according to the method 1000, the step of (block 1006) detecting the re-emission intensity 210 of the second light 206 is performed using the device 100. For example, the processing unit 114 is adapted to detect and process the re-emission intensity 210 of the second light 206.

In one or more examples, the method 1000 includes a step of (block 1008) determining the coverage metric 212 of the antimicrobial coating 202 based on the re-emission intensity 210 of the second light 206. In one or more examples, according to the method 1000, the step of (block 1008) determining the coverage metric 212 of the antimicrobial coating 202 is performed using the device 100. For example, the processing unit 114 is adapted to determine the coverage metric 212 of the antimicrobial coating 202 based on the re-emission intensity 210 of the second light 206.

In one or more examples, according to the method 1000, the step of (block 1004) detecting the second light 206 re-emitted from the antimicrobial coating 202 includes a step of (block 1010) capturing the illuminated image 118 of the surface 214 on which the antimicrobial coating 202 is applied and that is illuminated by the first light 108.

In one or more examples, according to the method 1000, the step of (block 1006) determining the re-emission intensity 210 of the second light 206 includes a step of (block 1012) analyzing the illuminated image 118 and a step of (block 1014) calculating the re-emission intensity 210 of the second light 206 represented in the illuminated image 118.

In one or more examples, according to the method 1000, the step of (block 1008) determining the coverage metric 212 of the antimicrobial coating 202 includes a step of (block 1016) correlating the re-emission intensity 210 of the second light 206 to one of the plurality of reference coverage metrics 130.

In one or more examples, the method 1000 includes a step of (block 1018) selecting the surface type 216 of the surface 214 and a step of (block 1020) selecting one of the plurality of sets 136 of correlation data 126 based on the surface type 216. Each one of the plurality of sets 136 of the correlation data 126 is associated with one of the plurality of reference surface types 134 and includes the plurality of reference coverage metrics 130 and the plurality of reference re-emission intensities 128 that correspond to the plurality of reference coverage metrics 130.

In one or more examples, according to the method 1000, the step of (block 1018) selecting the surface type 216 of the surface 214 is performed manually.

In one or more examples, according to the method 1000, the step of (block 1018) selecting the surface type 216 of the surface 214 is performed automatically by the device 100 and includes a step of (block 1022) capturing the unilluminated image 132 of the surface 214 on which the antimicrobial coating 202 is applied and that is not illuminated by the first light 108, a step of (block 1024) analyzing the unilluminated image 132, and a step of (block 1026) determining the surface type 216 of the surface 214. The surface type 216 of the surface 214 is automatically determined based on the analysis of the unilluminated image 132.

In one or more examples, the method 1000 includes a step of (block 1028) detecting the ambient light 218, a step of (block 1030) determining the ambient light intensity 222 of the ambient light 218, and a step of (block 1032) compensating the re-emission intensity 210 of the second light 206 for the ambient light intensity 222.

In one or more examples, according to the method 1000, the step of (block 1028) detecting the ambient light 218, the step of (block 1030) determining the ambient light intensity 222 of the ambient light 218, and the step of (block 1032) compensating the re-emission intensity 210 of the second light 206 for the ambient light intensity 222 are performed using the light detector 112 (e.g., the camera 116), the image processor 120 and/or the data processor 122.

In one or more examples, according to the method 1000, the step of (block 1028) detecting the ambient light 218 includes a step of (block 1034) capturing the unilluminated image 132 of the surface 214 on which the antimicrobial coating 202 is applied and that is not illuminated by the first light 108.

In one or more examples, according to the method 1000, the step of (block 1030) determining the ambient light intensity 222 of the ambient light 218 includes a step of (block 1036) analyzing the unilluminated image 132 and a step of (block 1038) calculating the ambient light intensity 222 of the ambient light 218. The ambient light intensity 222 of the ambient light 218 is calculated (e.g., determined or estimated within a specified value) based on the analysis of the unilluminated image 132.

In one or more examples, the method 1000 includes a step of (block 1040) selecting one of the plurality of sets 136 of correlation data 126 based on the ambient light intensity 222. Each one of the plurality of sets 136 of the correlation data 126 is associated with one of the plurality of reference ambient light intensities 156 and includes the plurality of reference coverage metrics 130 and the plurality of reference re-emission intensities 128 that correspond to the plurality of reference coverage metrics 130. In one or more examples, the step of (block 1032) compensating the re-emission intensity 210 of the second light 206 for the ambient light intensity 222 is achieved by the step of (block 1040) selecting one of the plurality of sets 136 of correlation data 126 based on the ambient light intensity 222.

In one or more examples, according to the method 1000, the step of (block 1032) compensating the re-emission intensity 210 of the second light 206 for the ambient light intensity 222 is achieved by performing (e.g., via the image processor 120 and the illumination processor 140) an analytical or computational analysis that compensates the value for the re-emission intensity 210 of the second light 206 for the value of the ambient light intensity 222 of the ambient light 218.

In one or more examples, according to the method 1000, the step of (block 1028) detecting the ambient light 218 is performed using the ambient light sensor 138. The step of (block 1030) determining the ambient light intensity 222 of the ambient light 218 includes a step of calculating the ambient light intensity 222 of the ambient light 218, for example, based on the electrical signal provided by the ambient light sensor 138. The step of (block 1032) compensating the re-emission intensity 210 of the second light 206 for the ambient light intensity 222 is achieved by performing (e.g., via the illumination processor 140) an analytical or computational analysis that compensates the value for the re-emission intensity 210 of the second light 206 for the value of the ambient light intensity 222 of the ambient light 218.

In one or more examples, the method 1000 includes a step of (block 1042) calculating the distance 224 between the device 100 (e.g., the light source 106 for the first light 108 and/or the light detector 112 for detecting the second light 206) and the surface 214. In one or more examples, according to the method 1000, the step of (block 1042) calculating the distance 224 is performed using the device 100. For example, the distance measurer 142 is adapted to determine the distance 224.

In one or more examples, the method 1000 includes a step of (block 1044) selecting one of the plurality of sets 136 of correlation data 126 based on the distance 224. Each one of the plurality of sets 136 of the correlation data 126 is associated with one of the plurality of reference distances 158 and includes the plurality of reference coverage metrics 130 and the plurality of reference re-emission intensities 128 that correspond to the plurality of reference coverage metrics 130.

In one or more examples, the method 1000 includes a step of (block 1046) optically filtering the second light 206 to transfer only the second wavelength 208 for detection.

In one or more examples, the method 1000 includes a step of (block 1048) providing at least one of the visual representation 150 of the coverage metric 212 and/or the audible indication 160 of the coverage metric 212.

In one or more examples, according to the method 1000, the step of (block 1008) determining the coverage metric 212 of the antimicrobial coating 202 includes a step of (block 1050) determining the thickness 234 of the antimicrobial coating 202 per unit of area of the surface 214.

In one or more examples, according to the method 1000, the step of (block 1008) determining the coverage metric 212 of the antimicrobial coating 202 includes a step of (block 1052) determining the concentration 236 of the antimicrobial coating 202 per unit of area of the surface 214.

In one or more examples, according to the method 1000, the step of (block 1008) determining the coverage metric 212 of the antimicrobial coating 202 includes a step of (block 1054) determining the efficacy 238 of the antimicrobial coating 202.

In one or more examples, according to the method 1000, the step of (block 1008) determining the coverage metric 212 of the antimicrobial coating 202 includes a step of (block 1056) determining the service life 240 (e.g., estimating the remaining service life expectancy) of the antimicrobial coating 202.

In one or more examples, the method 1000 include a step of (block 1058) providing (e.g., generating and displaying) the advisory action 162 based on the coverage metric 212.

Figure 8:
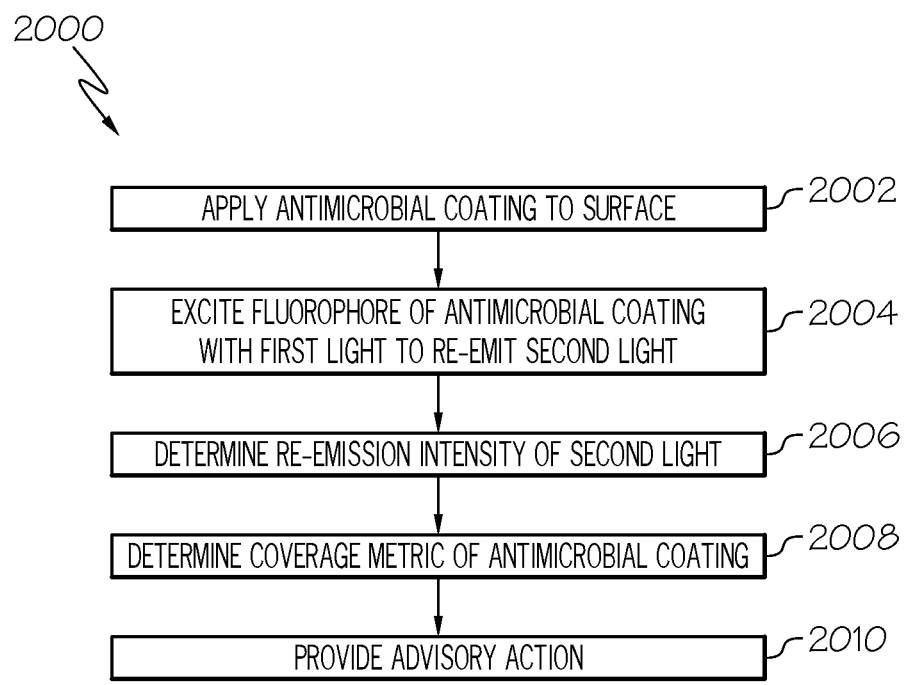
FIG. 8 is a flow diagram of an example of a method for sanitizing a surface

Referring now generally to FIGS. 1A, 1B and 2-6 and particularly to FIG. 8, by way of examples, the present disclosure is also directed to a method 2000 for sanitizing the surface 214. More particularly, the method 1000 is directed to applying the antimicrobial coating 202 on the surface 214, inspecting the surface 214, and determining the coverage metric 212 for the antimicrobial coating 202. In one or more examples, the method 1000 is implemented using the system 200.

Referring to FIG. 8, in one or more examples, the method 2000 includes a step of (block 2002) applying the antimicrobial coating 202 to at least a portion of the surface 214. In one or more examples, according to the method 2000, the step of (block 2002) applying the antimicrobial coating 202 is performed using the device 100. For example, the antimicrobial coating 202 is applied using the applicator 232.

The antimicrobial coating 202 includes the fluorophore 204 that re-emits the second light 206 having the second wavelength 208 in response to excitation by the first light 108. The second wavelength 208 of the second light 206 (e.g., blue light) is different than the first wavelength 110 of the first light 108 (e.g., ultraviolet light).

In one or more examples, the method 2000 includes a step of (block 2004) exciting the fluorophore 204 in response to the first light 108, having the first wavelength 110, such that the antimicrobial coating re-emits the second light 206 having the second wavelength 208, which is different than the first wavelength 110.

In one or more examples, according to the method 2000, the step of (block 2004) exciting the fluorophore 204 includes a step of directing the first light 108 having the first wavelength 110 at the surface 214 (e.g., block 1002 of the method 1000 shown in FIG. 7). In one or more examples, the method 2000 includes a step of detecting the second light 206 re-emitted from the antimicrobial coating 202 (e.g., block 1004 of the method 1000 shown in FIG. 7).

In one or more examples, the method 2000 includes a step of (block 2006) detecting, processing, and/or determining the re-emission intensity 210 of the second light 206. In one or more examples, the step of (block 2006) detecting the re-emission intensity 210 of the second light 206 is performed in a manner that is substantially similar to the corresponding step described for the method 1000 (e.g., block 1006 of the method 1000 shown in FIG. 7).

In one or more examples, the method 2000 includes a step of (block 2008) determining the coverage metric 212 of the antimicrobial coating 202 based on the re-emission intensity 210 of the second light 206. In one or more examples, the step of (block 2008) determining the coverage metric 212 of the antimicrobial coating 202 is performed in a manner that is substantially similar to the corresponding step described for the method 1000 (e.g., block 1008 of the method 1000 shown in FIG. 7).

In one or more examples, the method 2000 include a step of (block 2010) providing the advisory action 162 based on the coverage metric 212.

In one or more examples, the method 2000 may include additional steps performed in a manner substantially similar to the steps described for the method 1000. As an example, the method 2000 includes steps for selecting the surface type 216 and selecting one of the plurality of sets 136 of correlation data 126 based on the surface type 216 (e.g., block 1016 and block 1018 of the method 1000 shown in FIG. 7). As another example, the method 2000 includes steps for detecting the ambient light 218, determining the ambient light intensity 222 of the ambient light 218, selecting one of the plurality of sets 136 of correlation data 126 based on the ambient light intensity 222, and/or compensating the re-emission intensity 210 of the second light 206 for the ambient light intensity 222 (e.g., block 1026, block 1028, block 1030, and block 1038 of the method 1000 shown in FIG. 7). As another example, the method 2000 includes a step for providing at least one of the visual representation 150 of the coverage metric 212 and/or the audible indication 160 of the coverage metric 212 (e.g., block 1046 of the method 1000 shown in FIG. 7).

In one or more examples, the antimicrobial coating 202 includes an antimicrobial compound and nanostructures or antimicrobial nanoworms. In one or more examples, a surface coated with the antimicrobial coating 202 responds to environmental conditions of a droplet and surrounding external conditions. For example, an antimicrobial coated surface can respond to one or more environmental triggers, such as temperature, pH, salinity concentration, and/or light, to aid in the capture and killing of microbes. In one or more examples, a chemical composition and functionality of the antimicrobial coating 202 can be selected to enhance the capturing and killing of microbes. For example, an antimicrobial coated surface can be chemically modified with a carboxylic acid group, an alkyne, a pyridine, a dopamine, a thiolactone, a biotin, an azide, a peptide sequence (including one or more amino acids and/or combinations thereof), a nucleic acid sequence (including one or more nucleic acids and/or combinations thereof), a sugar sequence (including one or more monosugars, polysugars, and/or combinations thereof), a protease, a glycanase, a grafted polymer, quaternized amine groups, derivatives thereof, and/or combinations thereof, to capture/kill a broad range of microbes or to capture/kill a certain microbe, such as in response to a certain outbreak of a virus.

In one or more examples, the antimicrobial coating 202 is non-toxic. For examples, an antimicrobial coated surface is antimicrobial without being toxic to humans, animals, and/or plants.

In one or more examples, the antimicrobial compounds of the antimicrobial coating 202 are covalently bonded. Since the antimicrobial coating 202 is strongly adhered to the surface 214, the antimicrobial compounds of the antimicrobial coated surface are prevented from being ingested or absorbed by skin into the human body.

In one or more examples, the antimicrobial coating 202 can be washable by being able to be washed and re-used. For example, the antimicrobial coated surface can be washed with water (e.g., rinsed), cleaning agents (e.g., detergents, soaps, and surfactants), sanitizers, and/or disinfectants. The antimicrobial coated surface can be washed to renew the antimicrobial coated surface by removing captured or killed microbes from antimicrobial compounds of the antimicrobial coating 202.

In one or more examples, the antimicrobial coating 202 includes a copolymer of a macro chain transfer agent (macroCTA) polymer units and alkene units. A macroCTA polymer is a polymer formed by reversible addition-fragmentation chain-transfer (RAFT) utilizing a RAFT agent in the polymerization of one or more ethylenically unsaturated monomers. In one or more examples, the RAFT agent is incorporated in the macroCTA polymer which can be further polymerized with the addition of reactants.

In one or more examples, the polymer 250 (e.g., the macroCTA polymer units) of the antimicrobial coating 202 contains light-responsive monomers and/or functional groups in any suitable manner. Examples of light-responsive monomers and/or functional groups include those with chromophoric functional groups. Chromophoric functional groups are any functional groups that are sensitive to electromagnetic radiation (e.g., visible or non-visible light). The term "visible light" as used herein is defined as electromagnetic radiation having a wavelength from 380 nm to 750 nm. The term "non-visible light" as used herein is defined as electromagnetic radiation having a wavelength shorter than 380 nm (such as gamma rays, x-rays, ultraviolet) or longer than 750 nm (such as infrared, microwaves, radio waves). Examples of chromophoric functional groups include groups that can be or cause isomerization between a trans to a cis form; groups that can be or cause transition from a relatively non-polar hydrophobic, non-ionized state to a hydrophilic ionic state; and/or groups that are polymerized with other monomer or comonomer units in response to electromagnetic radiation. Example of chromophoric functional groups include azide-containing fluorescent dyes capable of being functionalized into the macroCTA polymer units through a CUAAC reaction, such as 3-azido-7-hydroxycoumarin, Azide-BDP-FL, 5-FAM-Azide, 6-FAM-Azide, Picolyl-Azide-5/6-FAM, AF488-Azide, AF488-Picolyl-Azide, 110-PEG3-Azide, 5-SIMA-Azide, 5-TAMRA-Azide, 5/6-TAMRA-PEG3-Azide, Picolyl-Azide-5/6-TAMRA, Cy3-Azide, Sulfo-Cy3-Azide, Picolyl-Azide-Sulfo-Cy3, AF546-Azide, AF546-Picolyl-Azide, AF555-Azide, AF555-Picolyl-Azide, 5/6-Texas Red-PEG3-Azide, AF594-Azide, AF594-Picolyl-Azide, Cy5-Azide, Sulfo-Cy5-Azide, Picolyl-Azide-Sulfo-Cy5, AF647-Azide, AF647-Picolyl-Azide, Cy5.5-Azide, Picolyl-Azide-Cy5.5, Cy7-Azide, Picolyl-Azide-Cy7.

Figure 9:
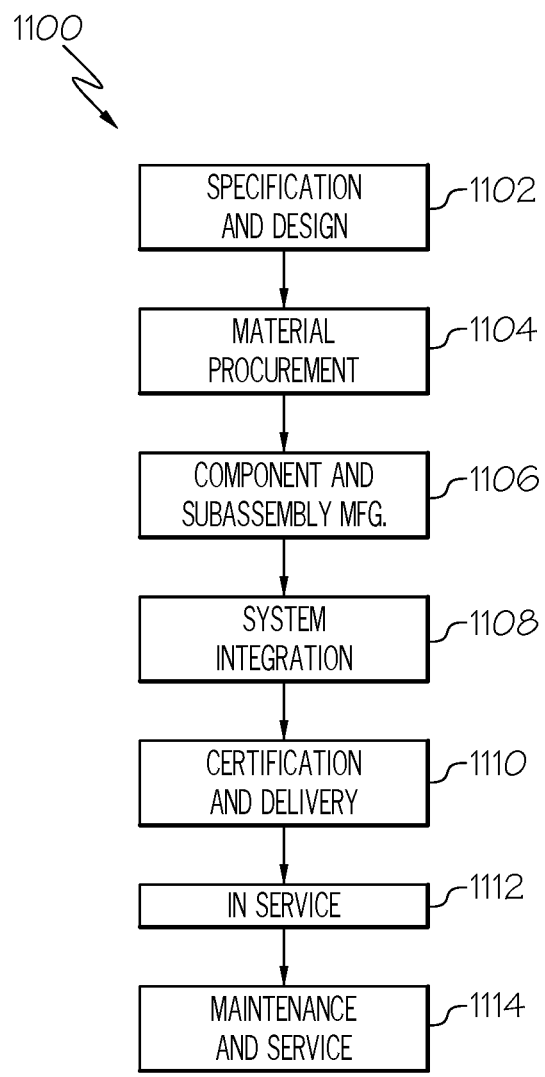
FIG. 9 is a flow diagram of an example of an aircraft manufacturing and service method.
Figure 10:
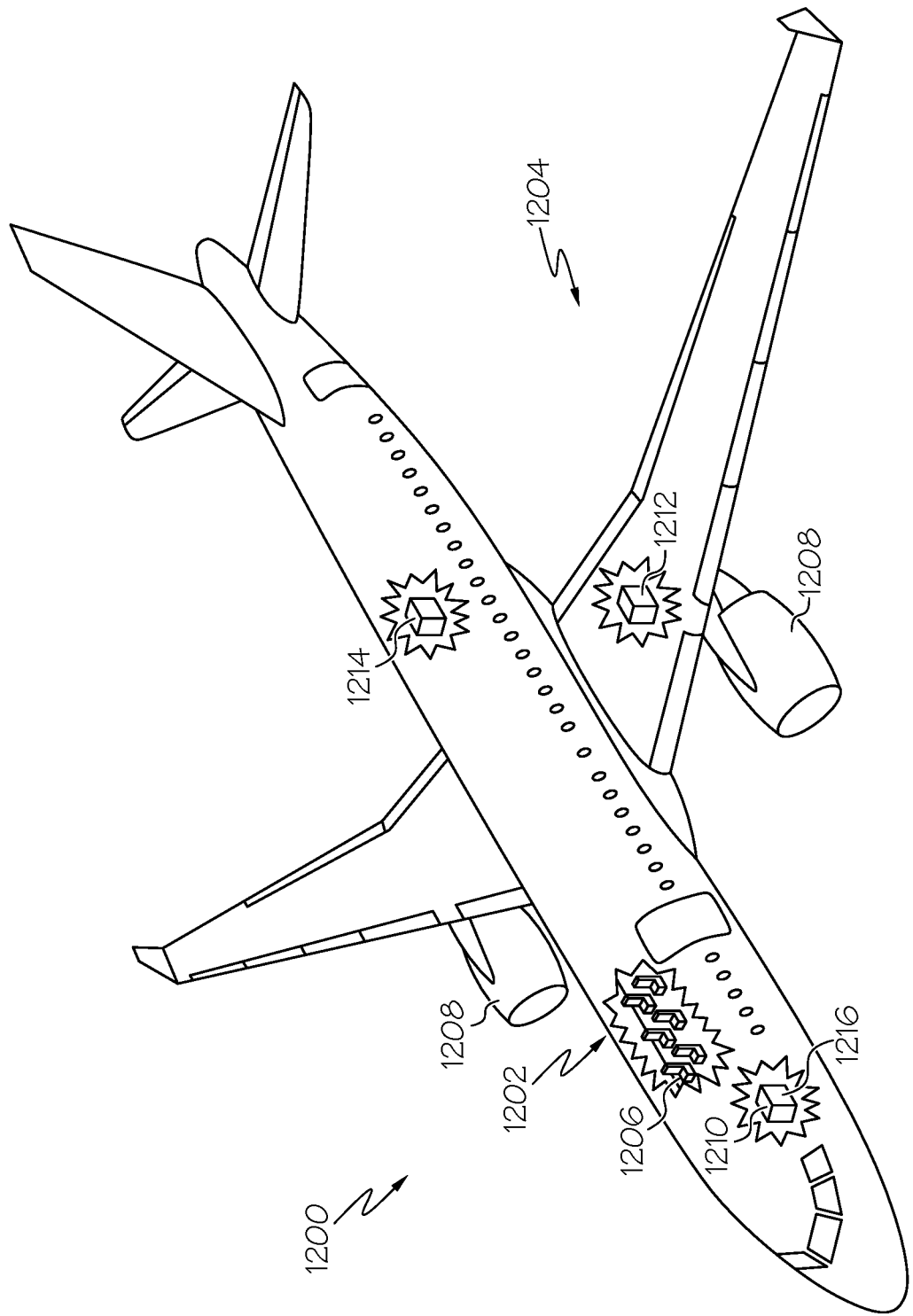
FIG. 10 is a schematic illustration of an example of an aircraft.

Referring now to FIGS. 9 and 10, examples of the device 100, the system 200, the method 1000, and the method 2000 may be related to, or used in the context of, an aircraft manufacturing and service method 1100, as shown in the flow diagram of FIG. 9 and an aircraft 1200, as schematically illustrated in FIG. 10. For example, the aircraft 1200 and/or the aircraft production and service method 1100 may utilize the system 200 and the method 2000 for sanitizing surfaces (e.g., interior surfaces) of the aircraft 1200 and the device 100 and the method 1000 for detecting antimicrobial coatings applied to the surfaces.

Referring to FIG. 10, examples of the aircraft 1200 may include an airframe 1202 having the interior 1206. The aircraft 1200 also includes a plurality of high-level systems 1204. Examples of the high-level systems 1204 include one or more of a propulsion system 1208, an electrical system 1210, a hydraulic system 1212, an environmental system 1214, and a communication system 1216. In other examples, the aircraft 1200 may include any number of other types of systems, such as a flight control system, a guidance system, a weapons system, and the like. In one or more examples, the surface 214 is any one of various surfaces on the interior 1206 of the aircraft 1200. For example, as illustrated in FIG. 6, the surface 214 may be a surface of a seat, a seat try, an armrest, an interior wall, and the like of the passenger cabin, flight cabin, or lavatory of the aircraft 1200.

Referring to FIG. 9, during pre-production, the method 1100 includes specification and design of the aircraft 1200 (block 1102) and material procurement (block 1104). During production of the aircraft 1200, component and subassembly manufacturing (block 1106) and system integration (block 1108) of the aircraft 1200 take place. Thereafter, the aircraft 1200 goes through certification and delivery (block 1110) to be placed in service (block 1112). Routine maintenance and service (block 1114) includes modification, reconfiguration, refurbishment, etc. of one or more systems of the aircraft 1200.

Each of the processes of the method 1100 illustrated in FIG. 9 may be performed or carried out by a system integrator, a third party, and/or an operator (e.g., a customer). For the purposes of this description, a system integrator may include, without limitation, any number of spacecraft manufacturers and major-system subcontractors; a third party may include, without limitation, any number of vendors, subcontractors, and suppliers; and an operator may be an airline, leasing company, military entity, service organization, and so on.

Examples of the device 100, the system 200, the method 1000, and the method 2000 shown and described herein, may be employed during any one or more of the stages of the manufacturing and service method 1100 shown in the flow diagram illustrated by FIG. 9. In an example, application and/or inspection of the antimicrobial coating 202 using the system 200 and/or the device 100 and/or according to the methods 1000, 2000 may form a portion of component and subassembly manufacturing (block 1106) and/or system integration (block 1108). Further, application and/or inspection of the antimicrobial coating 202 using the system 200 and/or the device 100 and/or according to the methods 1000, 2000 may be utilized in a manner similar to components or subassemblies prepared while the aircraft 1200 is in service (block 1112). Also, application and/or inspection of the antimicrobial coating 202 using the system 200 and/or the device 100 and/or according to the methods 1000, 2000 may be utilized during system integration (block 1108) and certification and delivery (block 1110). Similarly, application and/or inspection of the antimicrobial coating 202 using the system 200 and/or the device 100 and/or according to the methods 1000, 2000 may be utilized, for example and without limitation, while the aircraft 1200 is in service (block 1112) and during maintenance and service (block 1114).

Although an aerospace example is shown, the examples and principles disclosed herein may be applied to other industries, such as the automotive industry, the space industry, the construction industry, and other design and manufacturing industries. Accordingly, in addition to aircraft, the examples and principles disclosed herein may apply to sanitizing surfaces and inspecting antimicrobial coatings applied to surfaces of other types of vehicles (e.g., land vehicles, marine vehicles, space vehicles, etc.), stand-alone structures, high-traffic surfaces, and other high-contact surfaces.

For examples, the antimicrobial coating 202 and the device 100 and system 200 and associated methods 1000 and 2000 may be used to sanitize and inspect surfaces of many types of platforms. A platform having surface, upon which antimicrobial coating may be applied, may be, for example, a mobile platform, a stationary platform, a land-based structure, an aquatic-based structure, and a space-based structure. More specifically, a platform may be an aircraft, a surface ship, a tank, a personnel carrier, a train, a spacecraft, a space station, a satellite, a submarine, an automobile, a power plant, a bridge, a dam, a house, a manufacturing facility, a building, and any other suitable type of platform.

The preceding detailed description refers to the accompanying drawings, which illustrate specific examples described by the present disclosure. Other examples having different structures and operations do not depart from the scope of the present disclosure. Like reference numerals may refer to the same feature, element, or component in the different drawings. Throughout the present disclosure, any one of a plurality of items may be referred to individually as the item and a plurality of items may be referred to collectively as the items and may be referred to with like reference numerals. Moreover, as used herein, a feature, element, component, or step preceded with the word "a" or "an" should be understood as not excluding a plurality of features, elements, components or steps, unless such exclusion is explicitly recited.

Illustrative, non-exhaustive examples, which may be, but are not necessarily, claimed, of the subject matter according to the present disclosure are provided above. Reference herein to "example" means that one or more feature, structure, element, component, characteristic, and/or operational step described in connection with the example is included in at least one aspect, embodiment, and/or implementation of the subject matter according to the present disclosure. Thus, the phrases "an example," "another example," "one or more examples," and similar language throughout the present disclosure may, but do not necessarily, refer to the same example. Further, the subject matter characterizing any one example may, but does not necessarily, include the subject matter characterizing any other example. Moreover, the subject matter characterizing any one example may be, but is not necessarily, combined with the subject matter characterizing any other example.

As used herein, a system, apparatus, device, structure, article, element, component, or hardware "configured to" perform a specified function is indeed capable of performing the specified function without any alteration, rather than merely having potential to perform the specified function after further modification. In other words, the system, apparatus, device, structure, article, element, component, or hardware "configured to" perform a specified function is specifically selected, created, implemented, utilized, programmed, and/or designed for the purpose of performing the specified function. As used herein, "configured to" denotes existing characteristics of a system, apparatus, structure, article, element, component, or hardware that enable the system, apparatus, structure, article, element, component, or hardware to perform the specified function without further modification. For purposes of this disclosure, a system, apparatus, device, structure, article, element, component, or hardware described as being "configured to" perform a particular function may additionally or alternatively be described as being "adapted to" and/or as being "operative to" perform that function.

Unless otherwise indicated, the terms "first," "second," "third," etc. are used herein merely as labels, and are not intended to impose ordinal, positional, or hierarchical requirements on the items to which these terms refer. Moreover, reference to, e.g., a "second" item does not require or preclude the existence of, e.g., a "first" or lower-numbered item, and/or, e.g., a "third" or higher-numbered item.

As used herein, the phrase "at least one of", when used with a list of items, means different combinations of one or more of the listed items may be used and only one of each item in the list may be needed. For example, "at least one of item A, item B, and item C" may include, without limitation, item A or item A and item B. This example also may include item A, item B, and item C, or item B and item C. In other examples, "at least one of" may be, for example, without limitation, two of item A, one of item B, and ten of item C; four of item B and seven of item C; and other suitable combinations. As used herein, the term "and/or" and the "/" symbol includes any and all combinations of one or more of the associated listed items.

For the purpose of this disclosure, the terms "coupled," "coupling," and similar terms refer to two or more elements that are joined, linked, fastened, attached, connected, put in communication, or otherwise associated (e.g., mechanically, electrically, fluidly, optically, electromagnetically) with one another. In various examples, the elements may be associated directly or indirectly. As an example, element A may be directly associated with element B. As another example, element A may be indirectly associated with element B, for example, via another element C. It will be understood that not all associations among the various disclosed elements are necessarily represented. Accordingly, couplings other than those depicted in the figures may also exist.

As used herein, the term "approximately" refers to or represent a condition that is close to, but not exactly, the stated condition that still performs the desired function or achieves the desired result. As an example, the term "approximately" refers to a condition that is within an acceptable predetermined tolerance or accuracy, such as to a condition that is within 10% of the stated condition. However, the term "approximately" does not exclude a condition that is exactly the stated condition. As used herein, the term "substantially" refers to a condition that is essentially the stated condition that performs the desired function or achieves the desired result.

FIGS. 1-6 and 10, referred to above, may represent functional elements, features, or components thereof and do not necessarily imply any particular structure. Accordingly, modifications, additions and/or omissions may be made to the illustrated structure. Additionally, those skilled in the art will appreciate that not all elements, features, and/or components described and illustrated in FIGS. 1-6 and 10, referred to above, need be included in every example and not all elements, features, and/or components described herein are necessarily depicted in each illustrative example. Accordingly, some of the elements, features, and/or components described and illustrated in FIGS. 1-6 and 10 may be combined in various ways without the need to include other features described and illustrated in FIGS. 1-6 and 10, other drawing figures, and/or the accompanying disclosure, even though such combination or combinations are not explicitly illustrated herein. Similarly, additional features not limited to the examples presented, may be combined with some or all of the features shown and described herein. Unless otherwise explicitly stated, the schematic illustrations of the examples depicted in FIGS. 1-6 and 10, referred to above, are not meant to imply structural limitations with respect to the illustrative example. Rather, although one illustrative structure is indicated, it is to be understood that the structure may be modified when appropriate. Accordingly, modifications, additions and/or omissions may be made to the illustrated structure. Furthermore, elements, features, and/or components that serve a similar, or at least substantially similar, purpose are labeled with like numbers in each of FIGS. 1-6 and 10, and such elements, features, and/or components may not be discussed in detail herein with reference to each of FIGS. 1-6 and 10. Similarly, all elements, features, and/or components may not be labeled in each of FIGS. 1-6 and 10, but reference numerals associated therewith may be utilized herein for consistency.

In FIGS. 7-9, referred to above, the blocks may represent operations, steps, and/or portions thereof and lines connecting the various blocks do not imply any particular order or dependency of the operations or portions thereof. It will be understood that not all dependencies among the various disclosed operations are necessarily represented. FIGS. 7-9 and the accompanying disclosure describing the operations of the disclosed methods set forth herein should not be interpreted as necessarily determining a sequence in which the operations are to be performed. Rather, although one illustrative order is indicated, it is to be understood that the sequence of the operations may be modified when appropriate. Accordingly, modifications, additions and/or omissions may be made to the operations illustrated and certain operations may be performed in a different order or simultaneously. Additionally, those skilled in the art will appreciate that not all operations described need be performed.

Further, references throughout the present specification to features, advantages, or similar language used herein do not imply that all of the features and advantages that may be realized with the examples disclosed herein should be, or are in, any single example. Rather, language referring to the features and advantages is understood to mean that a specific feature, advantage, or characteristic described in connection with an example is included in at least one example. Thus, discussion of features, advantages, and similar language used throughout the present disclosure may, but do not necessarily, refer to the same example.

The described features, advantages, and characteristics of one example may be combined in any suitable manner in one or more other examples. One skilled in the relevant art will recognize that the examples described herein may be practiced without one or more of the specific features or advantages of a particular example. In other instances, additional features and advantages may be recognized in certain examples that may not be present in all examples. Furthermore, although various examples of the device 100, the system 200, the method 1000, and the method 2000 have been shown and described, modifications may occur to those skilled in the art upon reading the specification. The present application includes such modifications and is limited only by the scope of the claims.

What is claimed is:

1. A device for detecting an antimicrobial coating applied to a surface, the antimicrobial coating comprising a polymer, an antimicrobial agent bonded to the polymer, and a fluorophore bonded to at least one of the polymer and the antimicrobial agent, the device comprising:

a portable housing;

a light source that is disposed within the portable housing and that emits a first light having a first wavelength, wherein the coating comprises a fluorophore of the antimicrobial coating re-emits a second light having a second wavelength, which is different than the first wavelength, in response to excitation by the first light;

a light detector that is disposed within the portable housing and that receives the second light re-emitted from the coating; and a distance measurer that is coupled to the portable housing and that calculates a measured distance between the light source and the surface; and a processing unit that is disposed within the portable housing and that is operatively coupled to the light detector and the distance measurer, wherein;

the processing unit comprises a data processor and a memory coupled to the data processor;

the memory stores a plurality of reference re-emission intensities, a plurality of reference distances, and a plurality of reference coverage metrics; and the data processor is adapted to:

detect calculate a detected re-emission intensity of the second light received by the light detector;

correlate the detected re-emission intensity to one of the reference re-emission intensities;

correlate the measured distance to one of the reference distances;

correlate the one of the reference re-emission intensities and the one of the reference distances to one of the reference coverage metrics; and determine a coverage metric of the coating based on the re-emission intensity of the second light one of the reference coverage metrics.

2. The device of claim 1, wherein the light detector comprises a camera that captures an illuminated image of the surface on which the antimicrobial coating is applied and that is illuminated by the first light.

3. The device of claim 2, wherein the light detector further comprises a bandpass lens that transmits only the second light at the second wavelength to the camera.

4. The device of claim 2, wherein the processing unit further comprises an image processor that analyzes the illuminated image to calculate the re-emission intensity of the second light represented in the illuminated image.

5. The device of claim 4, wherein:
the camera captures an unilluminated image of the surface on which the antimicrobial coating is applied and that is not illuminated by the first light;
the image processor analyzes the unilluminated image to determine a surface type of the surface;
the memory stores a plurality of reference surface types; and
the data processor is adapted to:
correlate the surface type to one of the reference surface types; and
correlate the one of the reference re-emission intensities, the one of the reference distances, and the one of the reference surface types to the one of the reference coverage metrics.

6. The device of claim 4, wherein:
the camera captures an unilluminated image of the surface on which the antimicrobial coating is applied and that is not illuminated by the first light;
the image processor analyzes the unilluminated image to calculate an ambient light intensity of ambient light;
the memory stores a plurality of reference ambient light intensities and sets of the correlation data;
each one of the sets of the correlation data corresponds to one of the plurality of reference ambient light intensities; and
the data processor is adapted to:
correlate the ambient light intensity to one of the reference ambient light intensities; and
correlate the one of the reference re-emission intensities, the one of the reference distances, and the one of the reference ambient light intensities to the one of the reference coverage metrics.

7. The device of claim 4, wherein:
the camera captures an unilluminated image of the surface on which the antimicrobial coating is applied and that is not illuminated by the first light;
the image processor analyzes the unilluminated image to determine an ambient light intensity of ambient light received by the light detector; and
the processing unit further comprises an illumination processor that compensates the re-emission intensity of the second light for the ambient light intensity.

8. The device of claim 1, further comprising an ambient light sensor that is disposed within the portable housing and that detects ambient light,
wherein the processing unit is operatively coupled to the ambient light sensor and further comprises an illumination processor that calculates an ambient light intensity of the ambient light and that compensates the re-emission intensity of the second light for the ambient light intensity.

9. A system for sanitizing a surface, the system comprising:
an antimicrobial coating that is appliable to the surface, wherein the antimicrobial coating comprises a fluorophore that, in response to excitation by a first light at a first wavelength, re-emits a second light at a second wavelength, which is different than the first wavelength; and
a device for detecting the antimicrobial coating on the surface, wherein the device comprises:
a portable housing;
a light source that is disposed within the portable housing and that emits the first light at the first wavelength;
a light detector that is disposed within the portable housing and that receives the second light re-emitted from the antimicrobial coating;
an optical filter configured to block light at a wavelength that is different than the second wavelength from reaching the light detector; and
a processing unit that is disposed within the portable housing and that is operatively coupled to the light detector, wherein the processing unit is adapted to detect a re-emission intensity of the second light and to determine a coverage metric of the antimicrobial coating based on the re-emission intensity of the second light.

10. The system of claim 9, wherein the light detector comprises a camera that captures an illuminated image of the surface on which the antimicrobial coating is applied and that is illuminated by the first light.

11. The system of claim 10, wherein the optical filter comprises a bandpass lens that transmits only the second light at the second wavelength to the camera.

12. The system of claim 10, wherein the processing unit comprises an image processor that analyzes the illuminated image to calculate the re-emission intensity of the second light represented in the illuminated image.

13. The system of claim 12, wherein:
the processing unit further comprises:
data processor; and
a memory that is coupled to the data processor;
the memory stores correlation data, comprising a plurality of reference coverage metrics and a plurality of reference re-emission intensities that correspond to the plurality of reference coverage metrics; and
the data processor correlates the re-emission intensity of the second light to one of the plurality of reference coverage metrics to determine the coverage metric of the antimicrobial coating.

14. A method for detecting an antimicrobial coating applied to a surface, the method comprising steps of:
directing a first light emitted from a light source at the surface;
determining a measured distance between the light source and the surface;
detecting a second light re-emitted from the antimicrobial coating;
detecting determining a re-emission intensity of the second light; and
determining a coverage metric of the antimicrobial coating based on the re-emission intensity and the measured distance.

15. The method of claim 14, further comprising compensating the re-emission intensity of the second light for ambient light intensity.

16. The method of claim 14, further comprising:
determining a surface type of the surface; and
further determining the coverage metric of the antimicrobial coating based on the re-emission intensity, the measured distance, and the surface type.

17. The method of claim 14, wherein:
the first light has a first wavelength; and
the antimicrobial coating comprises a fluorophore that re-emits the second light having a second wavelength, which is different than the first wavelength, in response to excitation by the first light.

18. The method 17, further comprising:
optically filtering the second light; and
transmitting only the second wavelength for detection.

19. The method of claim 14, wherein the step of determining the coverage metric of the antimicrobial coating comprises determining a service life expectancy of the antimicrobial coating.

20. A method for sanitizing a surface, the method comprising:
applying an antimicrobial coating to at least a portion of the surface, wherein the antimicrobial coating comprises a fluorophore;
exciting the fluorophore in response to a first light, having a first wavelength, such that the antimicrobial coating re-emits a second light having a second wavelength, which is different than the first wavelength;
optically filtering the second light;
transmitting only the second wavelength for detection;
detecting the second light re-emitted from the antimicrobial coating;
determining a re-emission intensity of the second light; and
determining a coverage metric of the antimicrobial coating based on the re-emission intensity of the second light.

* * * * *